(12) United States Patent
Kosai

(10) Patent No.: US 10,738,324 B2
(45) Date of Patent: Aug. 11, 2020

(54) GROWTH-REGULATED VIRAL VECTOR CONTAINING THE AURORA KINASE PROMOTER

(75) Inventor: Ken-ichiro Kosai, Kagoshima (JP)

(73) Assignee: KAGOSHIMA UNIVERSITY, Kagoshima-Shi (JP)

(*) Notice: Subject to any disclaimer, the term of this patent is extended or adjusted under 35 U.S.C. 154(b) by 0 days.

(21) Appl. No.: 13/876,916

(22) PCT Filed: Sep. 29, 2011

(86) PCT No.: PCT/JP2011/072357
§ 371 (c)(1),
(2), (4) Date: Mar. 29, 2013

(87) PCT Pub. No.: WO2012/043710
PCT Pub. Date: Apr. 5, 2012

(65) Prior Publication Data
US 2013/0309203 A1 Nov. 21, 2013

(30) Foreign Application Priority Data
Sep. 30, 2010 (JP) ................. 2010-223150

(51) Int. Cl.
*C12N 15/86* (2006.01)
*C12N 7/00* (2006.01)
*A61K 35/76* (2015.01)
*C12N 9/12* (2006.01)

(52) U.S. Cl.
CPC .............. *C12N 15/86* (2013.01); *A61K 35/76* (2013.01); *C12N 7/00* (2013.01); *C12N 9/12* (2013.01); *C12N 2710/10332* (2013.01); *C12N 2830/008* (2013.01)

(58) Field of Classification Search
CPC ..................................................... C12N 15/86
See application file for complete search history.

(56) References Cited

U.S. PATENT DOCUMENTS

| | | |
|---|---|---|
| 2005/0031591 A1 | 2/2005 | Hamada |
| 2007/0036759 A1 | 2/2007 | Kosai et al. |
| 2009/0181907 A1* | 7/2009 | Kamizono et al. ............. 514/44 |

FOREIGN PATENT DOCUMENTS

| | | |
|---|---|---|
| JP | 2005-46101 A | 2/2005 |
| JP | 2007-508036 A | 4/2007 |
| JP | 2007-535315 A | 12/2007 |
| JP | WO 2008/120812 A1 * | 10/2008 ............ C12N 15/09 |
| WO | WO 03/025190 A1 | 3/2003 |
| WO | WO 2005/040156 A1 | 5/2005 |
| WO | WO 2005/103251 A2 | 11/2005 |
| WO | WO 2005/115476 A1 | 12/2005 |

OTHER PUBLICATIONS

Wakahara et al., (2008, Mol. Canc. Res., vol. 6(12), pp. 1937-1945).*
Furuhata et al. (2003, Molecular Therapy, vol. 7(3), pp. 366-374).*
STIC Seq. Report.*
Crane et al. (2003, Biology of the Cell, vol. 96, pp. 215-229).*
Chen et al. (2004, Cancer Gene Therapy, vol. 11, pp. 740-747) (Year: 2004).*
Bischoff et al., "A homologue of Drosophila aurora kinase is oncogenic and amplified in human colorectal cancers", The EMBO Journal, vol. 17, No. 11 (1998) pp. 3052-3065.
Carvajal et al., "Aurora Kinases: New Targets for Cancer Therapy", Clin. Cancer Res., vol. 12, No. 23 (2006) pp. 6869-6875.
English translation of International Preliminary Report on Patentabitty issued in PCT/JP2011/072357.
Kimura et el., "Cell cycle-dependent regulation of the human aurora B promoter", Biochemical and Biophysical Research Communications, vol. 316 (2004) pp. 930-936.
Murofushi et al., "Gene/virus medicines as innovative cancer treatment drug and regenerative medicines for liver diseases", Chemical Engineering, vol. 54, No. 1 (2009) pp. 32-38.
Tanaka et al., "Cell-cycle-dependent Regulation of Human aurora A Transcription is Mediated by Periodic Repression of E4TF1", J. Biological Chemistry, vol. 277, No. 12 (Issue of Mar. 22) (2002) pp. 10719-10726.
Tanaka et al., "Centrosomal Kinase AIK1 is Overexpressed in Invasive Ductal Carcinoma of the Breast", Cancer Research, vol. 59 (1999) pp. 2041-2044.

(Continued)

Primary Examiner — Thaian N. Ton
Assistant Examiner — David A. Montanari
(74) Attorney, Agent, or Firm — Birch, Stewart, Kolasch & Birch, LLP

(57) ABSTRACT

Disclosed is a vector, preferably a viral vector, containing a treatment factor and/or a nucleic acid encoding a cytotoxic factor under control of an Aurora kinase promoter. Also disclosed is a virus vector in which the promoter of a nucleic acid encoding a factor necessary to the replication or assembly of at least one virus is substituted by the Aurora kinase promoter. Also disclosed are a disease treatment agent, in particular a cancer treatment agent, which contains the aforementioned vector, and a clinical diagnostic agent, in particular a cancer diagnostic agent, which contains the vector containing the Aurora kinase promoter.

19 Claims, 7 Drawing Sheets

Specification includes a Sequence Listing.

(56) References Cited

OTHER PUBLICATIONS

Tatsuka et al., "Multinuclearity and Increased Ploidy Caused by Overexpression of the Aurora- and lpl1-like Midbody-associated Protein Mitotic Kinase in Human Cancer Cells", Cancer Research, vol. 58 (1998) pp. 4811-4816.
Wakahara et al., "EWS-FII1 Up-Regulates Expression of the Aurora A and Aurora B Kinases", Mol. Cancer Res., vol. 6, No. 12 (2008) pp. 1937-1945.
Zhou et al., "Tumour amplified kinase STK15/BTAK induces centrosome amplification, aneuploidy and transformation", Nature Genetics, vol. 20 (1998) pp. 189-193.
Japanese Office Action issued in Japanese Patent Application No. 2012-536543 dated May 12, 2015, with English translation.
Japanese Notice of Reasons for Rejection for Japanese Application No. 2012-536543, dated Dec. 15, 2015, with an English Translation.

\* cited by examiner

GROWTH-REGULATED VIRAL VECTOR CONTAINING THE AURORA KINASE PROMOTER

TECHNICAL FIELD

The present invention relates to vectors for treatment or prevention comprising Aurora kinase promoter(s). In particular, the invention relates to conditionally replicating virus vectors. More particularly, the present invention relates to adenovirus vectors that replicate specifically in cancer cells due to the Aurora kinase promoter and/or vectors that express cytotoxic or treatment factors specifically in cancer cells. The present invention also relates to a pharmaceutical composition for treatment of cancer comprising vectors having the Aurora kinase promoter.

BACKGROUND ART

Since 1991, many clinical studies have been conducted for gene therapies for cancer. These studies have succeeded in confirming its safety, however complete cure has not achieved yet and not all of cancer cells in patients' body could be killed. In the first half of 1990s, ex vivo gene therapies with retroviruses were carried out as gene therapy clinical studies for cancers, in that therapies cytokine genes or the like of inducing immunity were transfected into cancer cells in vitro and the cancer cells were inactivated their growth ability by radioactivity and then the cancer cells were returned into the patient's body. These ex vivo therapies were not achieved to give pharmaceutical products, because of many problems such as clinical maneuvers required and insufficient effects. In the 1990s, the in vivo gene therapy clinical studies were performed by direct administration of non-replicating vectors such as an adenovirus into tumor cells in vivo, and that proceed clinical development of the drugs for that therapies. In the 2000s, gene therapies using a cancer specific replicating virus has been studied and developed and the clinical studies have been carried out.

Recently, the inventor originally developed a technique that effectively produce cancer specific adenovirus vectors controlled by multiple factors as a next generation cancer specific replicating virus (Patent Document 1), and have preceded the development of the cancer gene therapy technique using the adenovirus vector (Patent Document 2).

The Aurora kinase was known as a kinase to control various events in cell division stages. Aurora-A, B, and C were identified presently. It has been reported that these kinases are expressed at higher levels in many human cancer cells than in normal cells (Non-patent Documents 1 to 4). However, those were only analytical reports for molecular functions, and there was no report for the Aurora kinase promoters investigated from a view of gene therapies. The gene therapy technique using a vector containing the Aurora kinase promoter has not been disclosed in the past, and there is no precedent case in which the promoter was used for other treatment use.

RELATED ART DOCUMENTS

Patent Documents

[Patent Document 1] Japanese Unexamined Patent Application Publication No. 2005-46101.
[Patent Document 2] WO2005/115476.

Non-Patent Documents

[Non-patent Document 1] Bishoff J R et al., EMBO J. 1998, 17(11): 3052-65.
[Non-patent Document 2] Zhou H et al., NAT Genet. 1998, 20(2): 189-93.
[Non-patent Document 3] Tatsuka M et al., Cancer Res. 1998, 58(21): 4811-6.
[Non-patent Document 4] Tanaka T et al., Cancer Res. 1999, 59(9): 2041-4.

DISCLOSURE OF THE INVENTION

Problems to be Solved by the Invention

Virus and gene therapies for cancers developed in the past still had problems in the specificity and efficacy. There are needs for a tool that enables more specific and more anticancer effective virus and gene therapies.

Means of Solving the Problems

The present inventor found that an Aurora kinase promoter exert enough transcriptional activities to be specific to cancer cells and to have enough anticancer effects, when the promoter is functionally binding to factors so that the promoters can control the factors which are necessary to replication or assembly of viruses and/or a nucleic acids encoding cytotoxic and/or treatment factors. The present inventor succeeded to produce a vector specific to cancer treatment or prevention using the promoter and accomplished the present invention.

More specifically, the present invention provides:

(1) an expression cassette containing an Aurora kinase promoter which functionally binds to a nucleic acids encoding cytotoxic or treatment factors;

(2) a vector containing the expression cassette according to (1);

(3) the vector according to (2), wherein the vector is a virus vector;

(4) the virus vector according to (3), wherein at least one promoters for a nucleic acids encoding a factor which is necessary for replication or assembly of virus is substituted with the Aurora kinase promoter or an exogenous promoter other than the Aurora kinase promoter;

(5) the virus vector according to (4), wherein at least one factors which is necessary for replication or assembly of virus is E1A, E1AΔ24, E1B, or E1BΔ55K;

(6) the virus vector according to (4), wherein the exogenous promoter other than the Aurora kinase promoter is a promoter of a factor which expression is specifically enhanced in the organ, a promoter of a factor which expression is specifically enhanced in cancer cells, or a promoter which can be constitutively expressed in mammals;

(7) the virus vector according to (6), wherein the promoter of the factor which expression is specifically enhanced in the organ is a promoter of albumin, α-fetoprotein, prostate-specific antigen (PSA), mitochondrial form creatine kinase (MCK), myelin basic protein (MB), glial fibrillary acidic protein (GFAP), or neuron-specific enolase (NSE);

(8) the virus vector according to (6), wherein the promoter of the factor which expression is specifically enhanced in the cancer cells is a promoter of telomerase reverse transcriptase (TERT), carcinoembryonic antigen (CEA), hypoxia responsive element (HRE), Grp78, L-plastin, hexokinase II, or survivin;

(9) the virus vector according to (6), wherein the promoter which can constitutively expressed in the mammals is a cytomegalovirus early gene promoter (CMV);

(10) a virus vector, wherein at least one promoter for nucleic acids encoding a factor which is necessary for replication or assembly of virus is substituted by an Aurora kinase promoter;

(11) the virus vector according to (10), wherein at least one promoter for the other nucleic acids encoding the factor necessary to the replication or assembly of virus is substituted by the exogenous promoter other than the Aurora kinase promoter;

(12) the virus vector according to (10) or (11), wherein at least one the factor which is necessary for replication or assembly of virus is selected from E1A, E1AΔ24, E1B, or E1BΔ55K;

(13) the virus vector according to any one of (10) to (12), wherein the virus vector comprises of an expression cassette including the Aurora kinase promoter or the exogenous promoter other than the Aurora kinase promoter that is operably linked to the nucleic acids encoding the cytotoxic or treatment factors;

(14) the virus vector according to (11) or (13), wherein the exogenous promoter other than the Aurora kinase promoter is the promoter of a factor which expression is specifically enhanced in the organ, the promoter of a promoter which expression is specifically enhanced in the cancer cells, or the promoter which can constitutively expressed in the mammals;

(15) the virus vector according to (14), wherein the promoter of the factor that expression is specifically enhanced in the organs may be a promoter of albumin, α-fetoprotein, prostate-specific antigen (PSA), mitochondrial form creatine kinase (MCK), myelin basic protein (MB), glial fibrillary acidic protein (GFAP), or neuron-specific enolase (NSE);

(16) the virus vector according to (14), wherein the promoter of the factor which expression is specifically enhanced in the cancer cells is a promoter of telomerase reverse transcriptase (TERT), carcinoembryonic antigen (CEA), hypoxia responsive element (HRE), Grp78, L-plastin, hexokinase II, or survivin;

(17) the virus vector according to (14), wherein a promoter which can constitutively expressed in mammals is a cytomegalovirus early gene promoter (CMV);

(18) the virus vector according to any one of (3) to (17), wherein the virus vector is a cytolytic virus vector;

(19) the virus vector according to claim 18), wherein the cytolytic virus vector is an adenovirus vector;

(20) the vector according to any one of (2) to (19), wherein the Aurora kinase promoter comprises of at least the 1363 to 1840 bases of the nucleotide sequence of SEQ ID NO: 1 or at least the 1595 to 2140 bases of the nucleotide sequence of SEQ ID NO: 3;

(21) a therapeutic agent for cancer comprising the vectors according to any one of (2) to (20);

(22) a method for treatment of cancer comprising administering the vector according to any one of (2) to (20) to mammals having cancer;

(23) a diagnostic agent comprising a vector including an Aurora kinase promoter; and

(24) the diagnostic agent according to (23), which is for a diagnosis of cancer.

Effects of the Invention

According to the present invention, highly specific and effective treatment of cancer is enabled.

MODE FOR CARRYING OUT THE INVENTION

The vector of the present invention is characterized that at least one promoters of nucleic acids encoding factors which is necessary for replication or assembly of virus is substituted by the Aurora kinase promoter, and/or that the vector comprises of the expression cassette wherein the Aurora kinase promoter is operably linked to nucleic acids encoding cytotoxic and/or treatment factors.

Promoters of human Aurora kinase A and B genes were isolated (Tanaka, M. et al., *J. Biol. Chem.*, 277(12):10719-26, 2002; Kimura, M. et al., *Biochem. Biophys. Res. Commun.*, 316:930-6, 2004), and the plasmid vectors to analyze functions of the promoters in which a reporter gene was inserted into the downstream of the promoters have been reported. However, there has been no report for a virus vector in which promoter(s) of nucleic acids encoding the factors which is necessary for virus replication or assembly is substituted with the Aurora kinase promoter, or a vector in which a nucleic acids encoding a protein or RNA which related to cytotoxicity or has treatment activities is operably linked to the Aurora kinase promoter, as well as treatment and preventive effects of those vectors. Also, a diagnostic usage of a vector in which a marker gene is operably linked to the Aurora kinase promoter has not been reported. Specifically, no application of the Aurora kinase focused on its specific expression is reported for use in production of a conditionally replicating virus specific for target diseases, especially for cancers, wherein the viruses are triggered to replicate depending on the Aurora kinase and the target disease cells are specifically killed, among many proteins reported for specific expression in the target disease cells such as cancer cells.

Figure 3:
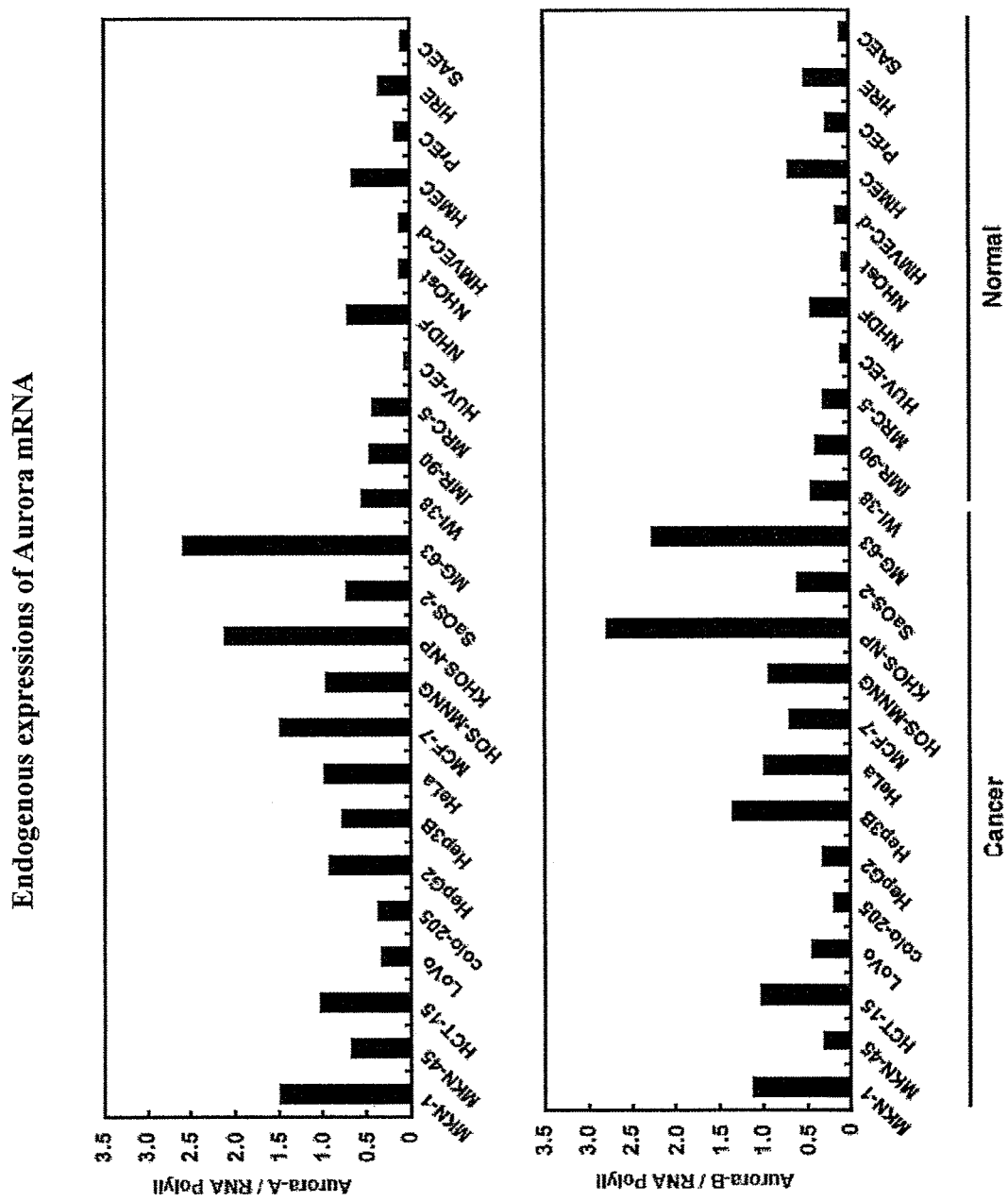
FIG. 3 shows graphs of the endogenous Aurora mRNA expressions in each cell. The data were corrected for the amount of type II polymerase mRNA.
Figure 4:
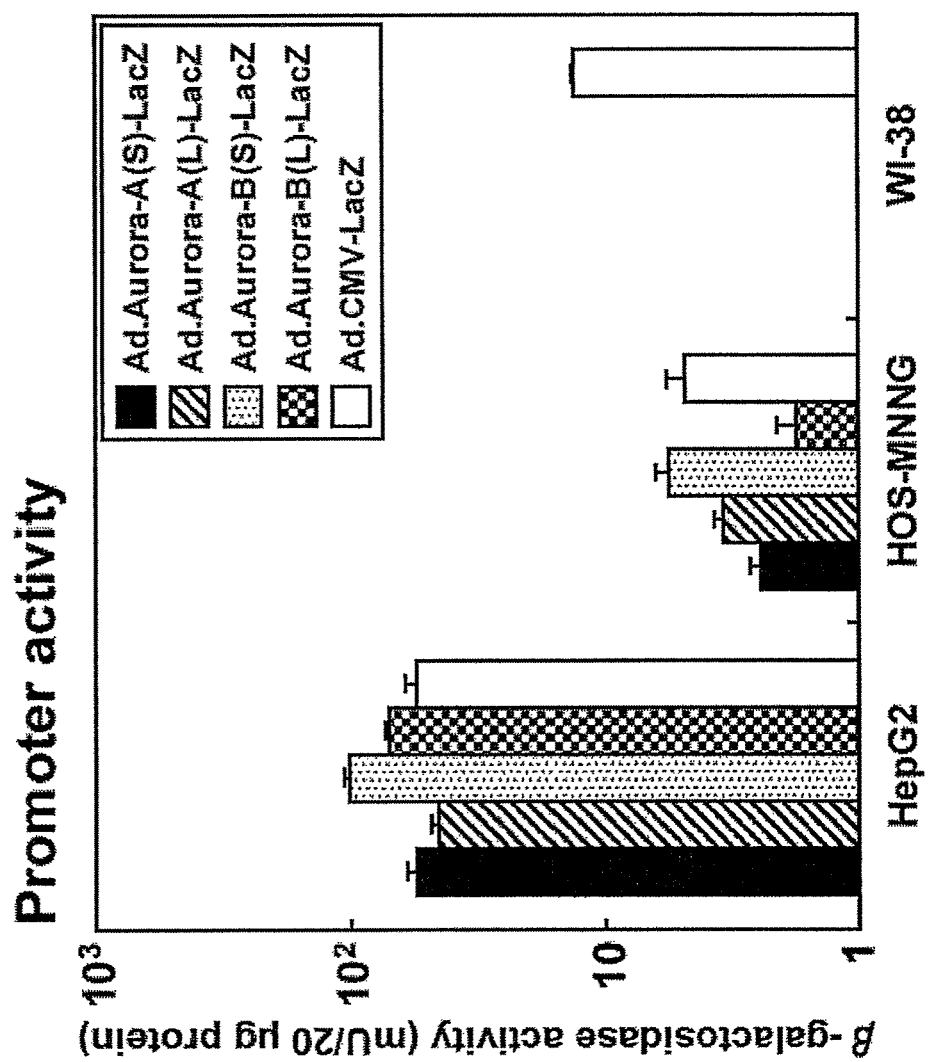
FIG. 4 is a graph which indicates the cancer specific high activities of the Aurora-A and Aurora-B promoters.

In particular, endogenous Aurora kinases are expressed at high level in some human cancer cells but also slightly expressed in human normal cells (for example, see FIG. 3). Therefore, the Aurora kinase promoters were expected to work on human cancer cells but also on human normal cells. Nevertheless, the present inventor found that the Aurora kinase promoter inserted into the vector of the present invention and exogenously transfected promotes expression of a gene linked to its downstream highly specifically in the target disease cells such as cancer cells, but do not show transcriptional activities at a detectable level in normal cells (for example, see FIG. 4). This high specificity of the Aurora kinase promoter could not be expected from the expression pattern of the endogenous Aurora kinase. In the present specification, a term "specific" dose not limitedly construed to the case in which no transcriptional activity can be confirmed in normal cells as shown in FIG. 4, but also includes a case in which the gene expression is promoted in normal cells within the level which is allowable in treatment.

The Aurora kinase promoter used for the vector of the present invention is not limited as long as promoters originated from genes belonging to an Aurora kinase family, and includes, for example, mammalian (human, monkeys, cattle, horses, pigs, dogs, cats, sheep, goats, rabbits, mice, rats or the like) orthologs of drosophila Aurora-A, Aurora-B and Aurora-C genes, preferably is the promoters of Aurora kinase-A or Aurora kinase-B genes originated from human or other mammals, more preferably is the promoters of human Aurora kinase-A or Aurora kinase-B genes. Depending on the mammals to be treated, the same species of the Aurora kinase promoter are preferable.

A nucleotide sequence length of the Aurora kinase promoter is not limited as long as being specific for target disease cells (such as cancer cells) and being able to activate the transcription of genes linked to its downstream to the extent to provide enough treatment effects on the target diseases. For example, promoter including following sequences, in the case of human Aurora kinase-A gene promoter, counting from the transcription start site (+1), the nucleotide sequence of positions −124 to +354 (the nucleotide sequence of SEQ ID NO: 2; 1363 to 1840 bases of the nucleotide sequence of SEQ ID NO: 1), in the case of the human Aurora kinase-B gene promoter, counting from the transcription start site (+1), the nucleotide sequence of positions −185 to +361 (the nucleotide sequence of SEQ ID NO: 4; 1595 to 2140 bases of the nucleotide sequence of SEQ ID NO: 3) can give the objective specificities and transcriptional activities (for example, see FIG. 4). Therefore, the human Aurora kinase gene promoter used for the vector of the present invention preferably comprising the 1363 to 1840 bases of the nucleotide sequence of SEQ ID NO: 1 and the 1595 to 2140 bases of the nucleotide sequence of SEQ ID NO: 3. There is no upper limit to the length of nucleotide sequence of the Aurora kinase promoter, but too long 5' upstream might adversely affect transcriptional activities or specificities of the promoters. For example, in the case of the human Aurora kinase-A gene promoter, counting from the transcription start site (+1), the nucleotide sequence of positions −1486 to +354 (the nucleotide sequence of SEQ ID NO: 1), in the case of the human Aurora kinase-B gene promoter, counting from the transcription start site (+1), the nucleotide sequence of positions −1779 to +361 (the nucleotide sequence of SEQ ID NO: 3) can give objective specificities and transcriptional activities (for example, see FIG. 4). In a preferred embodiment, 5' end of the human Aurora kinase promoter used for the vector of the present invention can be 1 to 1363 nucleotides of the nucleotide sequence of SEQ ID NO: 1, or 1 to 1595 nucleotides of the nucleotide sequence of SEQ ID NO: 3. In using the Aurora kinase promoter originated from other mammals, the preferable region can be selected in the same way.

The Aurora kinase promoter includes nucleic acids which can hybridize with a natural and mammal originated Aurora kinase promoter under a stringent condition having substantially same properties of the natural promoter. "Substantially same properties" means properties to promote a gene expression specifically in the target disease cells such as cancer cells, wherein the degree of transcriptional activities is preferably same (for example, approximately 0.5 to 2 times of the natural promoter), but the quantitative elements may be different as long as the gene expression is promoted at the level to achieve treatment activities to the target diseases. For example, in the case of human Aurora kinase-A or B promoter, nucleic acids which can hybridize with a complementary strand sequence of the nucleotide sequence of SEQ ID NO: 1 or 3 under the stringent condition can be used. As such nucleic acids, for example, the nucleic acids of the nucleotide sequence having an approximately 80% or more, preferably approximately 90% or more, more preferably approximately 95% or more, especially more preferably approximately 97% or more, the most preferably approximately 98% or more homology with the nucleotide sequence of SEQ ID NO: 1 or 3. The homology of nucleotide sequence in this specification can be calculated, for example, by using the homology computational algorithm, National Center for Biotechnology Information Basic Local Alignment Search Tool (NCBI BLAST) with the following conditions: the expected value is 10; gap is allowable; filtering is on; match score is 1; and miss match score is −3.

Hybridization can be carried out according to the known methods or the equivalent methods, such as the method described in *Molecular Cloning*, second edition (J. Sambrook et al., Cold Spring Harbor Lab. Press, 1989). When the commercial library is used, hybridization can be carried out according to the method described in the instruction manual attached. Hybridization can preferably be carried out under the high stringent condition. The stringent conditions are exemplarily shown as reaction conditions characterized by: (1) employing low-ionic strength and high temperature condition for washing, such as 0.015 M sodium chloride/ 0.0015 M sodium citrate/0.1% sodium dodecyl sulfate at 50° C.; (2) applying a denaturant like formamide at 42° C., such as 50% (v/v) formamide with 0.1% bovine serum albumin/ 0.1% ficoll/0.1% polyvinylpyrrolidone/50 mM sodium phosphate buffer (pH 6.5) containing 750 mM sodium chloride and 75 mM sodium citrate. The stringent conditions may also be as follows: 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 mg/ml), 0.1% SDS, and 10% dextran sulfate are used at 42° C., washed with 0.2×SSC and 50% formaldehyde at 55° C., and then perform a high stringency wash with 0.1×SSC containing EDTA at 55° C. The person skilled in the art can easily achieve the desired stringency by properly controlling the temperatures and ionic strength of a buffer or the like for hybridization reaction and/or wash according to factors such as probe lengths.

The Aurora kinase promoter can be prepared by cloning a genome DNA including the Aurora kinase promoter region from the genome DNA extracted from cells or tissues originated from human or other mammals (monkeys, cattle, horses, pigs, dogs, cats, sheep, goats, rabbits, mice, rats or the like) using the nucleic acids of the known Aurora kinase gene promoter sequence (for example, see Tanaka, M. et al., *J. Biol. Chem.*, 277(12):10719-26, 2002; Kimura, M. et al., *Biochem. Biophys. Res. Commun.*, 316:930-6, 2004) as a probe, cutting into DNA fragments having a desired part of promoter sequence with DNA degrading enzyme such as appropriate restriction enzyme, isolating with a gel electrophoresis, collecting a desired band, and purifying the DNA. Alternatively, a part of sequence of the Aurora kinase promoter can be amplified and isolated by performing PCR with a primer synthesized based on the known Aurora kinase gene promoter sequence using rough extract solution of the above cells or a genome DNA isolated from the solution as a template. For mammals in which the nucleotide sequence of the Aurora kinase promoter is unknown, the nucleotide sequence of the Aurora kinase promoter region of the mammals can be obtained by BLAST search on the genome DNA of the mammals using the Aurora kinase cDNA sequence of the mammals as a query.

Alternatively, the Aurora kinase promoter can be obtained by chemical synthesis of a nucleic acids based on the known Aurora kinase gene promoter sequence (for example, the nucleotide sequence of SEQ ID NO: 1 or 3) as nucleic acids containing all or a part of the known nucleotide sequence using the commercial DNA/RNA automatic synthesizer.

In one embodiment, the present invention relates to the expression cassette comprising the Aurora kinase promoter operably linked to nucleic acids encoding the cytotoxic or treatment factors, and to the vector comprising the expression cassette. The nucleic acids encoding the cytotoxic factors under control of the Aurora kinase promoter contained in the vector of the present invention may encode any protein or RNA as long as, for example, which can directly or indirectly kill the cells or at least inhibit the growth of the cells after transcription (or translation).

The treatment factor under control of the Aurora kinase promoter contained in the vector of the present invention may any protein (or RNA) as long as the factor directly or indirectly provides treatment effects to target diseases by function other than cytotoxic functions after translation (or transcription). For example, in the case that the target disease is a cancer, the cytotoxic or treatment factors include a cancer suppressor gene (such as p53, p21), a cytokine gene (such as GM-CSF, IL-2, IL-4, IFN), an apoptosis induction gene (such as Fas), a gene encoding component protein of the ion channel (such as sodium channel), a gene for protein which can damage cells by transforming a prodrug into a toxic agent (suicide gene) (such as HSV-thymidine kinase, cytosine deaminase), an antisense nucleic acids to a cancer responsible gene (such as an antisense nucleic acids to TGF-β or survivin), an angiostatic gene (such as a platelet factor IV, an angiostatin, an endostatin, a soluble VEGF receptor), miRNA having cancer suppression function or mimics thereof, an antisense nucleic acids against miRNA having cancer promoting function, an aptamer, a ribozyme or the like.

The nucleic acids encoding the cytotoxic or treatment factors can be isolated as cDNA from the cells or tissues that produce the nucleic acids by known methods and can operably linked to the downstream of the Aurora kinase promoter. The expression cassette comprising the nucleic acids encoding the cytotoxic or treatment factors under control of the Aurora kinase promoters preferably includes an appropriate polyadenylation sequence at the downstream of the nucleic acids or gene.

In the vectors comprising the expression cassette including the Aurora kinase promoters operably linked to the nucleic acids encoding the cytotoxic or treatment factors, the nucleic acids encoding the protein which is necessary for replication or assembly of the virus may be controlled by the Aurora kinase promoter or the exogenous promoter other than the Aurora kinase promoter. For example, a constitutive promoter can be used as the exogenous promoter other than the Aurora kinase promoters, including a promoter which can be constitutively expressed in mammals, such as a cytomegalovirus (CMV) origin promoter (such as CMV pre-early promoter), a human immunodeficiency virus (HIV) origin promoter (such as HIV LTR), a rous sarcoma virus (RSV) origin promoter (such as RSV LTR), a mouse mammary tumor virus (MMTV) origin promoter (such as MMTV LTR), a moloney mouse leukemia virus (MoMLV) origin promoter (such as MoMLV LTR), a herpes simplex virus (HSV) origin promoter (such as HSV thymidine kinase (TK) promoter), an SV40 origin promoter (such as SV40 early promoter), an Epstein-Barr virus (EBV) origin promoter, an adeno-associated virus (AAV) origin promoter (such as AAV p5 promoter), and adenovirus (AdV) origin promoter (Ad2 or Ad5 major late promoter) or the like; and a promoter for a gene encoding constitutive protein of mammals, such as a β-actin gene promoter, a PGK gene promoter, and a transferrin gene promoter. As the exogenous promoter other than the Aurora kinase promoter, promoters of genes which can be specifically expressed in target disease cells, promoters of factors which expression are specifically enhanced in target organ, or inducible promoters may be used. As promoters of factors which expression are specifically enhanced in organ, for example, promoter of albumin or α-fetoprotein which is specific in the liver etc.; promoter of prostate-specific antigen (PSA) which is specific in the prostate, promoter of mitochondrial form creatine kinase (MCK) which is specific to various organs such as muscle or brain, promoter of myelin basic protein (MB), glia fibrillary acidic protein (GFAP) or neuron-specific enolase (NSE) which is specific in the nervous system such as brain can be employed. In the case that the target disease is cancer, for example, promoters of factors which expression are specifically enhanced in the cancer cells can be used as the exogenous promoter other than the Aurora kinase promoter. For example, promoters specifically expressed only in cancer cells such as carcinoembryonic antigen (CEA) promoter (*Mol. Cell. Biol.*, 10(6), 2738-2748, 1990), E2F promoter (Neuman, E. et al., *Mol. Cell. Biol.*, 14(10), 6607-6615, 1994), and osteocalcin (OC) promoter (Morrison, N. A. et al., *Science*, 246, 1158-1161, 1989); promoters specific to malignant melanoma or fibrosarcoma or the like such as FLK-1 promoter (Xie, B. et al., *Br. J. Cancer*, 81, 1335-1343, 1999); promoters specific to lung cancers or the like such as VEGF promoter (Koshikawa, N. et al., *Cancer Res.*, 60, 2936-2941, 2000); promoters specific to small cell lung cancers or the like such as c-Myc promoter (Kumagai, T. et al., *Cancer Res.*, 354-358, 1996); promoters specific to ovarian cancers such as SLPI promoter (Garver, R. I. et al., *Gene Ther.*, 1, 46-50, 1994); promoters specific to prostate cancers such as PSA promoter (Latham, J. P. et al., *Cancer Res.*, 60, 334-342, 2000); promoters specific to malignant melanoma or the like such as Tyrosinase promoter (Vile, R. G. et al., *Cancer Res.*, 53, 962-967, 1993); promoters specific to breast cancers such as AP-2 promoter (Pandha, H. S. et al., *J. Clin. Oncol.*, 17, 2180-2189, 1999); promoters specific to many cancers involving brain cancers such as telomerase reverse transcriptase (TERT) promoter (Takakura, M. et al., *Cancer Res.*, 59, 551-557, 1999); and promoters specific to various cancers such as hypoxia responsive element (HRE) promoter, Grp78 promoter, L-plastin promoter, hexokinase II promoter, and survivin promoter can be employed. As the inducible promoter, for example, metallothionein-1 gene promoter can be used. In using the metallothionein-1 gene promoter, expression of virus protein can be induced specifically in the target disease cells at any time by administering inducing substances such as heavy metals including gold, zinc and cadmium, steroids such as dexamethasone, alkylating agents, chelating agents, and cytokines locally at the position of target disease cells at desirable time.

In another embodiment, the present invention relates to the conditionally replicating virus (CRV) vector specific to the target diseases site which is characterized that at least one promoter of nucleic acids encoding factors which is necessary for replication or assembly of virus is substituted with the Aurora kinase promoter (hereinafter referred to as "Aurora kinase promoter dependent CRV"). In other words, the present invention relates to the vector characterized that the vector is replicated specifically (superior to in normal cells) in target disease cells such as cancer cells. The virus vectors not only enable the viruses to proliferate specifically in target disease cells such as cancer cells, but also kill (lyse) the target disease cells as a result of replication. Moreover, the viruses released from the lysed cells infect peripheral disease cells which the vector still have not be transfected, which is repeated to transfect all disease cells in the focus with the vectors of the present invention and to obtain the treatment effects.

The Aurora kinase promoter dependent CRV of the present invention can be assembled by placing at least one nucleic acids encoding a protein which is necessary for replication or assembly of virus under control of the Aurora kinase promoter. "The factors necessary for replication or assembly of virus" means a gene encoding any of proteins which are necessary for self-replication of the virus such as component proteins of the virus, or a gene encoding any of proteins which are necessary for assembly of the virus. More specifically, the factor which is necessary for replication or assembly of the virus depends on the species of the viruses, and in the case of an adenovirus, the factor includes E1A, E1B, E2, and E4, or Rb binding region defective E1A (E1AΔ24), p53 binding region defective E1B (E1BΔ55K) and the like as described later, which are the early genes which regulate the transcription of the virus protein after start of transcription from early stage of the infection. Particularly, the E1A is transcribed at the beginning after the adenovirus infection, and the virus cannot replicate without expression of the E1A, so that the E1A is very suitable gene for controlling the virus replication to be specific in target disease sites such as cancers by using the Aurora kinase promoter. The similar effect can be obtained by controlling other early genes necessary for virus replication. Also, by controlling expression of late genes with the Aurora kinase promoter, the virus replication can be controlled specific in the target diseases sites such as cancers. The late genes are nucleic acids encoding the constitutive genes of the adenovirus such as L1, L2, L3, L4, L5 and the like which encode proteins constituting viral structure and are transcribed at the late stage after the infection, during cell division. As described above, in the Aurora kinase promoter dependent conditionally replicating virus vectors of the present invention, the gene encoding the virus protein which expression is controlled by the Aurora kinase promoter may be any virus genes as long as which is necessary for replication or assembly of the virus. The Aurora kinase promoter dependent conditionally replicating virus vector can be obtained by substituting the endogenous promoter of the nucleic acids encoding the protein which is necessary for replication or assembly of the virus with the Aurora kinase promoter. Preferably, in the conditionally replicating adenovirus vector of the present invention, the nucleic acids encoding the E1A and/or E1B, more preferably the nucleic acids encoding at least the E1A is under control of the Aurora kinase promoter.

The Aurora kinase promoter dependent CRV of the present invention transfected into cells cannot proliferate under the environment in which the Aurora kinase promoter is not activated (such as in normal cells), and the transfected cells are not damaged. On the other hand, when the Aurora kinase promoter dependent CRV of the present invention invade into the environment in which the Aurora kinase promoter is activated (such as in target disease cells), the virus proliferate and the cells are damaged due to the cytotoxicity of the virus protein. Then, the viruses are released from the lysed cells and infect the peripheral non-transfected cells one after another, which is repeated and finally the conditionally replicating vectors of the present invention are transfected to all disease cells in the focus.

By placing at least one nucleic acids encoding the protein which is necessary for replication or assembly of the virus under control of the Aurora kinase promoter, replication or assembly of the virus is limitedly occurred in the environment where the Aurora kinase promoter can be activated, and thus the nucleic acids encoding other proteins which are necessary for replication or assembly of virus may be placed under control of any exogenous promoter other than the Aurora kinase promoters. For example, as the exogenous promoter other than the Aurora kinase promoter, promoters which can constitutively express in mammals can be used, such as cytomegalovirus (CMV) origin promoter (such as CMV pre-early promoter), human immunodeficiency virus (HIV) origin promoter (such as HIV LTR), rous sarcoma virus (RSV) origin promoter (such as RSV LTR), mouse mammary tumor virus (MMTV) origin promoter (such as MMTV LTR), moloney mouse leukemia virus (MoMLV) origin promoter (such as MoMLV LTR), herpes simplex virus (HSV) origin promoter (such as HSV thymidine kinase (TK) promoter), SV40 origin promoter (such as SV40 early promoter), Epstein-Barr virus (EBV) origin promoter, adeno-associated virus (AAV) origin promoter (such as AAV p5 promoter), adenovirus (AdV) origin promoter (Ad2 or Ad5 major late promoter) or the like, and also constitutional promoters like promoters of genes of constitutional proteins of mammals, such as β-actin gene promoter, PGK gene promoter, and transferrin gene promoter can be used. As the exogenous promoter other than the Aurora kinase promoter, promoters of genes which can be specifically expressed in target disease cells, promoters of factors which expression are specifically enhanced in target organ, or inducible promoters may be used. As promoters of factors which expression are specifically enhanced in organ, for example, promoter of albumin or α-fetoprotein which is specific in the liver etc.; promoter of prostate-specific antigen (PSA) which is specific in the prostate, promoter of mitochondrial form creatine kinase (MCK) which is specific to various organs such as muscle or brain, promoter of myelin basic protein (MB), glia fibrillary acidic protein (GFAP) or neuron-specific enolase (NSE) which is specific in the nervous system such as brain can be employed. In the case that the target disease is cancer, for example, promoters of factors which expression are specifically enhanced in the cancer cells can be used as the exogenous promoter other than the Aurora kinase promoter. For example, promoters specifically expressed only in cancer cells such as carcinoembryonic antigen (CEA) promoter (*Mol. Cell. Biol.,* 10(6), 2738-2748, 1990), E2F promoter (Neuman, E. et al., *Mol. Cell. Biol.,* 14(10), 6607-6615, 1994), and osteocalcin (OC) promoter (Morrison, N. A. et al., *Science,* 246, 1158-1161, 1989); promoters specific to malignant melanoma or fibrosarcoma or the like such as FLK-1 promoter (Xie, B. et al., *Br. J. Cancer,* 81, 1335-1343, 1999); promoters specific to lung cancers or the like such as VEGF promoter (Koshikawa, N. et al., *Cancer Res.,* 60, 2936-2941, 2000); promoters specific to small cell lung cancers or the like such as c-Myc promoter (Kumagai, T. et al., *Cancer Res.,* 354-358, 1996); promoters specific to ovarian cancers such as SLPI promoter (Garver, R. I. et al., *Gene Ther.,* 1, 46-50, 1994); promoters specific to prostate cancers such as PSA promoter (Latham, J. P. et al., *Cancer Res.,* 60, 334-342, 2000); promoters specific to malignant melanoma or the like such as a Tyrosinase promoter (Vile, R. G. et al., *Cancer Res.,* 53, 962-967, 1993); promoters specific to breast cancers such as AP-2 promoter (Pandha, H. S. et al., *J. Clin. Oncol.,* 17, 2180-2189, 1999); promoters specific to many cancers involving brain cancers such as telomerase reverse transcriptase (TERT) promoter (Takakura, M. et al., *Cancer Res.,* 59, 551-557, 1999); and promoters specific to various cancers such as hypoxia responsive element (HRE) promoter, Grp78 promoter, L-plastin promoter, hexokinase II promoter, and survivin promoter can be employed. As the inducible promoter, for example, metallothionein-1 gene promoter can be used. In using the metallothionein-1 gene promoter, expression of virus protein can be induced specifically in the target disease cells at any time by administering inducing substances such as heavy metals including gold, zinc and cadmium, steroids such as dexamethasone, alkylating agents, chelating agents, and cytokines locally at the position of target disease cells at desirable time.

When placing two or more of nucleic acids encoding proteins which are necessary for replication or assembly of virus under control of the Aurora kinase promoter, the promoter used may be same or different. For example, the Aurora kinase-A and B promoters can be used in one vector in combination. The Aurora kinase promoter dependent CRV may further include an expression cassette comprising the Aurora kinase promoter which is operably linked to nucleic acids encoding cytotoxic or treatment factors.

The virus vector of the present invention may lack regions which are essential for induction of cell environment which is necessary for proliferation of the virus in normal cells but which is unnecessary for proliferation of the virus in target disease cells. For example, when the target disease is cancers, in normal cells it is necessary to inactivate Rb and p53 for progression of the cell cycle which enable proliferation of adenoviruses, whereas in cancer cells cell cycle has been already progressed and thus Rb binding region of E1A and p53 biding region of E1B are not necessary for proliferation of the adenoviruses. In using adenovirus, the virus can proliferate specifically in cancer cell by deleting the E1A 24 KDa region (E1AΔ24), the E1B 55 KDa region (E1BΔ55K), or the E1B 19 KDa region (E1BΔ19). This types of virus vector can proliferate specifically in cancer cells without placing nucleic acids encoding proteins which are necessary for replication of the viruses under control of cancer cell specific promoters such as the Aurora kinase promoter. The virus vector of the present invention includes the virus vector in which nucleic acids encoding cytotoxic or treatment factors are operably linked to and under control of the Aurora kinase promoter, wherein any nucleic acids encoding proteins which is necessary for replication or assembly of the virus are not under control of the Aurora kinase promoter, and wherein the regions which are essential to induce the necessary cell environment for virus proliferation in normal cells but are not necessary for virus proliferation in target disease cells (such as the E1A 24 KDa, E1B 55 KDa, and/or E1B 19 KDa regions) are deleted. Of course, the nucleic acids encoding the virus protein which is deleted the region(s) essential to induce the necessary cell environment for virus proliferation in normal cells but not necessary for virus proliferatin in target disease cells (such as the E1A24 KDa, E1B55 KDa, and/or E1B19 KDa regions) may be placed under control of the Aurora kinase promoter, or nucleic acids encoding protein(s) which is necessary for virus proliferation other than the above deleted virus proteins may be placed under control of the Aurora kinase promoter. In the case the nucleic acids encoding the virus protein which is deleted the regions essential to induce the cell environment necessary for virus proliferation in normal cells but not necessary for virus proliferation in target disease cells (such as the E1A24KDa, E1B55KDa, and/or E1B19KDa regions) is under control of the Aurora kinase promoter, or any of nucleic acids encoding the protein which is necessary for virus proliferation other than the above deleted virus proteins are placed under control of the Aurora kinase promoter, the conditionally replicating virus vector of the present invention does not need to further contain the treatment factor under control of the Aurora kinase promoter.

The vector of the present invention may further contain a replication origin for self-replication in host cells and selective marker genes for selecting transformed cells (genes for obtaining resistance to drugs such as tetracycline, ampicillin, kanamycin, hygromycin, phosphinothricin and the like, genes complementary to nutrient requiring mutant, and the like).

The diseases for which the vector of the present invention can be used as a treatment vector are not particularly limited as long as a causal factor of the disease is cells wherein the Aurora kinase promoter can show an activity which can promote enough gene expression to treat the disease, and preferably is a cancer. The cancers include, but not limited to, renal cell carcinoma, fibrosarcoma, myxosarcoma, liposarcoma, chondrosarcoma, osteosarcoma, chordoma, angiosarcoma, endothelial sarcoma, lymphangiosarcoma, endothelial lymphangiosarcoma, synovioma, mesothelioma, Ewing's tumor, leiomyosarcoma, rhabdomyosarcoma, colon cancer, pancreatic cancer, breast cancer, ovarian cancer, prostate cancer, squamous cell carcinoma, basal cell carcinoma, adenocarcinoma, syringocarcinoma, sebaceous adenocarcinoma, papillocarcinoma, papillary adenocarcinoma, cystadenocarcinoma, medullary carcinoma, bronchogenic carcinoma, liver cancer, cholangiocarcinoma, choriocarcinoma, seminoma, embryonal carcinoma, Wilms' tumor, cervical cancer, testicle tumor, lung cancer, small cell lung cancer, bladder cancer, epithelial cancer, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, acute lymphocytic leukemia, acute myelogenous leukemia, chronic leukemia, polycythemia vera, lymphoma, and multiple myeloma. The preferable target cancers include the liver cancer and osteosarcoma.

The vector of the present invention may be a virus vector or a non-virus vector, and preferably is virus vector such as the adenovirus, retrovirus, adeno-associated virus, herpes virus, herpes simplex virus, lentivirus, vaccinia virus, poxvirus, polio virus, sindbis virus, and Sendai virus. The adenovirus has benefits, such that the gene is able to be transfected with high efficiency, to be transfected to non-dividing cells, and the transgenes are rarely inserted into the host chromosome. Particularly, by the development of a gutted (gutless) vector that the full length of the adenovirus genome except for the packaging signal (4) are substituted with the transgenes, problems of the immunogenicity in first generation vectors were solved, and which enabled long time sustained expression of the transgene. Similarly, the adeno-associated virus is preferable for the virus vector of the present invention, because the gene transfection efficiency is relatively high, the genes can be transfected to non-dividing cells, and long-time sustained expression of the transgenes administered in vivo in animal experiments is reported.

Figure 1:
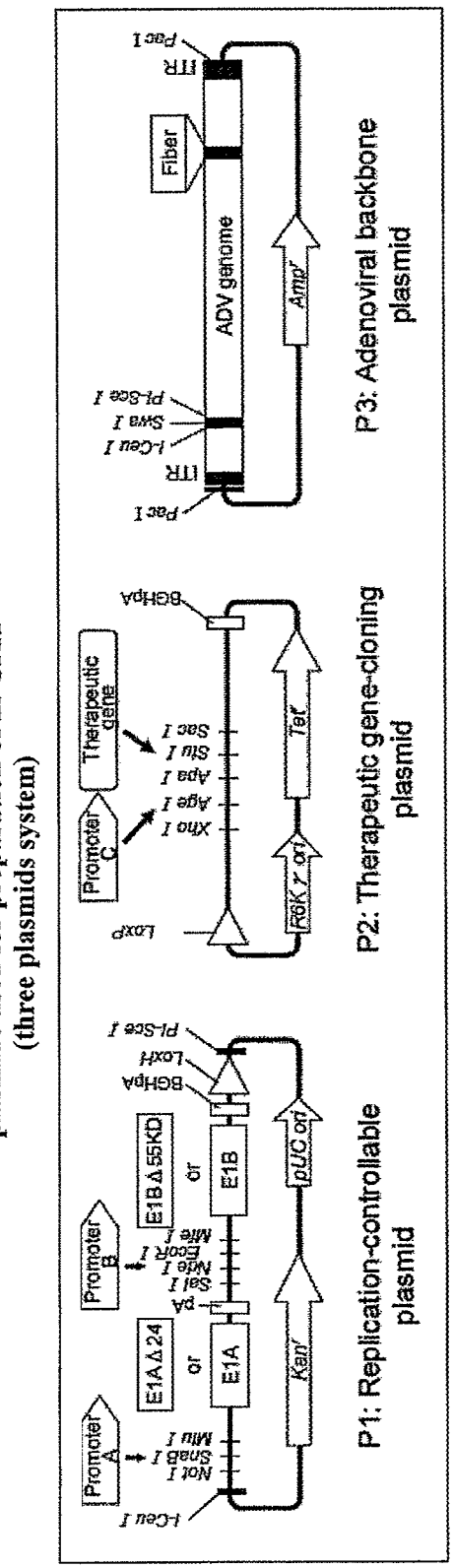
FIG. 1 shows schematic diagrams of the plasmid structures used for producing conditionally replicating adenoviruses with multiple tumor specific factors (m-CRAs).

In a preferred embodiment of the present invention, the Aurora kinase promoter is used as a part of the conditionally replicating recombinant adenovirus with multiple factors specific to cancer cells (m-CRA, JP2005-046101A and WO2005/012536) developed by the present inventor. FIG. 1 shows an example of a plasmid vector appropriately used for assembling the m-CRA. In FIG. 1, the Aurora kinase promoters are used as promoters A and/or B out of the plasmid vector P1, and the Aurora kinase promoter or any other desired promoter such as target tissue specific promoter or constitutive promoter can be used as a promoter C of the plasmid vector P2 (for control of expression of the cytotoxic or treatment factors). As the target tissue specific promoter, if the target tissue is cancer cells, for example, various promoters described above that are specifically expressed only in cancer cells can be used. As the cytotoxic or treatment factors controlled by the promoter C, if the target disease is a cancer, for example, various cytotoxic or treatment factors described above can be used.

Figure 2:
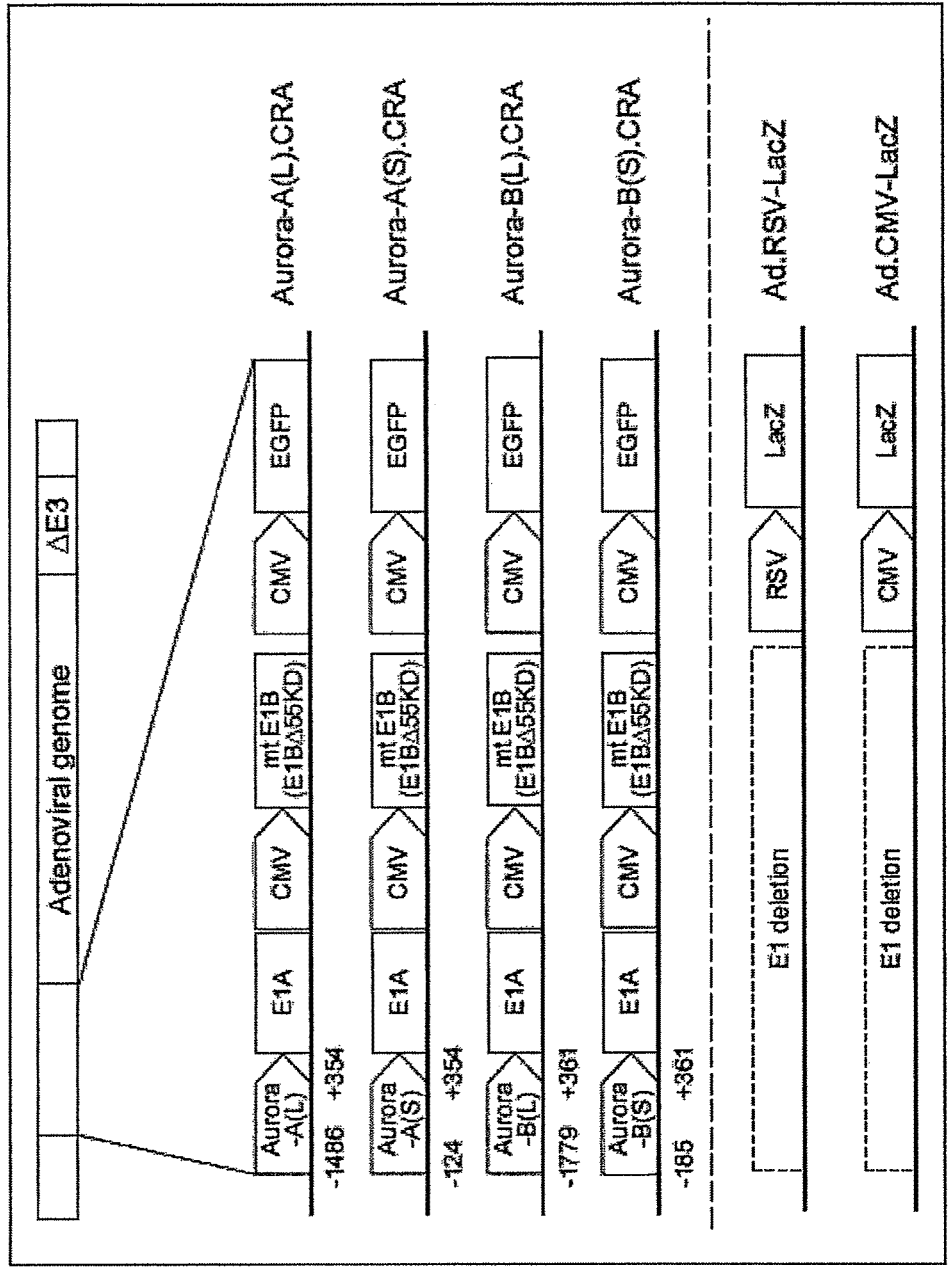
FIG. 2 shows schematic diagrams of the gene structures of the cancer specific conditionally replicating adenoviruses (CRAs) in which virus replications are controlled by the Aurora kinase promoters and schematic diagrams of the gene structures of replication incompetent (E1 defective) adenoviruses which express LacZ under control of constitutive expression promoters (Ad.RSV-LacZ and Ad.CMV-LacZ).

The specific embodiment shown in the examples described below provides the plasmid vector P1 comprising an E1A gene operably linked to the Aurora kinase promoter (wherein the 24 KDa region may be deleted) and an E1B gene operably linked to the constitutive promoter (such as the CMV promoter) (wherein the 19 KDa or 55 KDa region may be deleted), the plasmid vector P2 comprising the reporter gene (as a model system for cytotoxic or treatment factors) operably linked to the constitutive promoter (such as the CMV promoter), and a backbone plasmid P3 comprising the adenovirus genome wherein the E1 region is deleted (that may have a mutation to be specific to target cells in fiber genes). These three plasmids are appropriately fused in combination by using the Cre recombinase/LoxP system, and an objective plasmid is selected by using the drug resistance gene and on contained in each plasmid to obtain the conditionally replicating adenovirus (CRA) vector plasmid specific to cancer cells comprising an Aurora kinase promoter—E1A expression cassette, a constitutive promoter—E1B expression cassette and a constitutive promoter—cytotoxic or treatment factor expression cassette. Then, the CRA vector can be produced by transfecting the vector into the cell strain complementary to the E1A (such as 293 cells). In FIG. 2, proliferation of the m-CRA vector is controlled by two factors of the promoter for controlling the E1A expression (Aurora-A or B) and the E1B gene (E1B Δ55K). More strict proliferation and expression by multiple factors can be enabled by replacing the E1A gene, the promoter for control of the E1B expression, the promoter for control of the cytotoxic or treatment factor, the cytotoxic or treatment factor, and fiber genes of the back bone with the other elements.

The non-virus vectors of the present invention comprise the expression cassette including cytotoxic or treatment factors under control of the Aurora kinase promoter. As the vector, an *Escherichia coli* origin plasmid (such as pBR322, pBR325, pUC12, pUC13), a *Bacillus subtilis* origin plasmid (such as pUB110, pTP5, pC194), a yeast origin plasmid (such as pSH19, pSH15), an animal cell expression plasmid (such as pA1-11, pXT1, pRc/CMV, pRc/RSV, pcDNAI/Neo) may be used. Herein, "cytotoxic factors" and "treatment factors" means as the same as described above, and when the target disease is a cancer, for example, the various cancer treatment factors described above can be used.

In addition to the above, the non-virus vector of the present invention can contain an enhancer, splicing signal, a poly(A) adding signal, a selection marker, and an SV40 replication origin, if desired. For example, the selection marker includes a dihydrofolate reductase (dhfr) gene [methotrexate (MTX) resistance], an ampicillin resistance (Amp$^r$) gene, a neomycin resistance (Neo$^r$) gene (G418 resistance), and the like.

When the non-virus vector is used, the vector can be transfected by using polymeric molecule carriers such as poly-L-lysine-nucleic acids complex or by encapsulating in the liposome. The liposome is a capsule of tens to hundreds nm of particle size constituting of the phospholipids. The vectors such as the plasmid comprising cytotoxic or treatment factors under control of the Aurora kinase promoter can be encapsulated in the liposome. Alternatively, the vector can directly transfected into target cells using particle gun method.

The conditionally replicating virus vector specific to target diseases of the present invention, wherein at least one promoter for a nucleic acids encoding factor which is necessary for replication or assembly of virus is substituted with Aurora kinase promoter, or the vector of the present invention comprising cytotoxic and/or treatment factor(s) under control of the Aurora kinase promoter can be proliferated or can express the cytotoxic and/or treatment factors specifically in target disease cells such as cancer cells. Consequently, the vector can be used as a treatment agent for the target disease, preferably for a cancer, after mixing with a pharmaceutically acceptable carrier, if required, and preparing as various pharmaceutical formulations such as an injectable solution. Herein, as the pharmaceutically acceptable carrier, various organic or inorganic carrier substances conventionally used as the drug formation materials can be used and contained, for example, as excipients, lubricants, bounding agent and disintegrant in a solid preparation; and as a solvent, a solubilizing agent, a suspending agent, an isotonizing agent, a buffer agent and a soothing agent in a liquid preparation. The pharmaceutical formulation additives such as an antiseptic, an antioxidant, a colorant and a sweeting agent may be also used, if required.

Preferable examples of the excipients include, for example, lactose, saccharose, D-mannitol, D-sorbitol, starch, pregelatinized starch, dextrin, microcrystalline cellulose, low-substituted hydroxylpropylcellulose, sodium carboxy methylcellulose, gum arabic, pullulan, light anhydrous silicic acids, synthetic aluminum silicate, and magnesium aluminometasilicate.

Preferable examples of the lubricants include, for example, aluminum monostearate, calcium stearate, talc, and colloidal silica.

Preferable examples of the bounding agents are, for example, pregelatinized starch, sucrose, gelatin, gum Arabic, methylcellulose, carboxy methylcellulose, sodium carboxy methylcellulose, microcrystalline cellulose, saccharose, D-mannitol, trehalose, dextrin, pullulan, hydroxylpropylcellulose, hydroxypropyl methylcellulose, and polyvinylpyrrolidone.

Preferable examples of the disintegrants include, for example, lactose, saccharose, starch, carboxy methylcellulose, carboxy methylcellulose calcium, croscarmellose sodium, sodium carboxymethyl starch, light anhydrous silicic acids, and low-substituted hydroxyl propylcellulose.

Preferable examples of the solvents include, for example, water for injection, physiological saline, Ringer's solution, alcohol, propylene glycol, polyethylene glycol, sesame oil, corn oil, olive oil, and cottonseed oil.

Preferable examples of the solubilizing agents include, for example, propylene glycol, polyethylene glycol, D-mannitol, trehalose, benzyl benzoate, ethanol, tris aminometane, cholesterol, triethanolamine, sodium carbonate, sodium citrate, sodium salicylate, and sodium acetate.

Preferable examples of the suspending agents include, for example, surfactants such as stearyl triethanol amine, sodium lauryl sulfate, lauryl amino propionate, lecithin, benzalkonium chloride, benzethonium chloride, glyceryl monostearate; hydrophilic macromolecules such as polyvinyl alcohol, polyvinylpyrrolidone, sodium carboxy methylcellulose, methylcellulose, hydroxymethylcellulose, hydroxyethylcellulose, hydroxyl propylcellulose; polysorbates, and castor oil polyethoxylated hydrogenated.

Preferable examples of the isotonizing agents include, for example, sodium chloride, glycerin, D-mannitol, D-sorbitol, and dextrose.

Preferable examples of the buffer agents are, for example, buffer solution such as phosphate, acetate, carbonate, and citrate.

Preferable examples of the soothing agents include, for example, benzyl alcohol.

Preferable examples of the antiseptics include, for example, p-hydroxybenzoic esters, chlorobutanol, benzyl alcohol, phenethyl alcohol, phenethyl acids, and sorbic acids.

Preferable examples of the antioxidants include, for example, sulfite, and ascorbate.

Preferable examples of the colorants include, for example, water-soluble coal tar dye (food colors such as food red No. 2 and 3, food yellow No. 4 and 5, and food blue No. 1 and 2), water insoluble lake pigments (such as aluminum salt of the water-soluble coal tar dye), and natural dye (such as beta-carotene, chlorophyll, and colcothar).

Preferable examples of the sweeting agents include, for example, saccharin sodium, glycyrrhizinate dipotassium, aspartame, and stevia.

The disease treatment agent comprising the vector of the present invention can be administrated either by an ex vivo method or an in vivo method, and in vivo method is preferable. In the ex vivo method, target cells of the treatment subject animals (allogeneic or heterologous animals to the treatment subject animals) are taken out of the body, cultured and then returned (or transplanted) into the body. In the in vivo method, the vector is directly administered to the body of the subject animals. In the ex vivo method, the vector can be transfected to the target cells by a microinjection method, a calcium phosphate transfection, a polyethylene glycol method, an electroporation, and the like. In the in vivo method, the pharmaceutical formation is administrated via an injection, a catheter, a balloon catheter, a local injection, and a transplantation of an implant integrated the vector of the present invention to the lesion site, or the like.

The dose of the disease treatment agent comprising the vector of the present invention can be differ depending on type of the vectors, promoter activities in target cells, a kind of treatment factors, an administration route, severity of the disease, animal species of the administration subject, drug receptivity of the administration subject, weight, ages, and the like. For example, if the cancer specific conditionally replicating adenovirus is used as the virus vector, $1\times10^{10}$ to $10^{12}$ particle/tumor of the virus particles can be criteria of the administration, because the conventional clinical study for cancer gene therapy showed the safety with the same dose (*Molecular Therapy*, 18: 429-434, 2010). If the non-virus vector encapsulated in the liposome is used, 666 µg of DNA can be a criterion because the clinical study using cynomolgus monkeys of approximately 4 kg weight showed the safety with same dose of intravenous administration. For example, an adult dosage can be approximately 2 to 10 mg, preferably, approximately 5 to 8 mg.

The present invention also provides the clinical diagnostic agent comprising the vectors including the Aurora kinase promoter. The disease that can be diagnosed using the diagnostic agent of the present invention are not limited as long as it is a disease wherein a causal factor of the disease is cells in which the Aurora kinase promoter can show specific activity to promote expression of the gene linked to its downstream, that is superior to in normal cells, and preferably is a cancer. As the gene operably linked to the downstream of the Aurora kinase promoter is not particularly limited as long as the gene expression can be easily monitored, and includes, for example, but not limited to, various reporter genes such as a luciferase gene, a green fluorescent protein (GFP) gene, and a β-galactosidase (LacZ) gene. In using the above mentioned conditionally replicating virus vector as a therapeutic agent, the gene expression can be monitored from the cytotoxicity as an index.

For example, the vector comprising the Aurora kinase promoter is transfected into the cells taken from of the lesion site of a subject suspicious for cancer, and expression of the reporter genes in cells or cytolysis are detected. Preferably, compared with control normal cells in which said vector are transfected, significantly higher expression level of the reporter genes in the cells or cytolysis than those of normal cells leads diagnosis the subject to have cancer with high possibility.

The cancer that can be diagnosed with the diagnostic agent of the present invention includes, for example, but not limited to, renal cell carcinoma, fibrosarcoma, myxosarcoma, liposarcoma, chondrosarcoma, osteosarcoma, chordoma, angiosarcoma, endothelial sarcoma, lymphangiosarcoma, endothelial lymphangiosarcoma, synovioma, mesothelioma, Ewing's tumor, leiomyosarcoma, rhabdomyosarcoma, colon cancer, pancreatic cancer, breast cancer, ovarian cancer, prostate cancer, squamous cell carcinoma, basal cell carcinoma, adenocarcinoma, syringocarcinoma, sebaceous adenocarcinoma, papillocarcinoma, papillary adenocarcinoma, cystadenocarcinoma, medullary carcinoma, bronchogenic carcinoma, liver cancer, cholangiocarcinoma, choriocarcinoma, seminoma, embryonal carcinoma, Wilms' tumor, cervical cancer, testicle tumor, lung cancer, small cell lung cancer, bladder cancer, epithelial cancer, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, acute lymphocytic leukemia, acute myelogenous leukemia, chronic leukemia, polycythemia vera, lymphoma, and multiple myeloma. The preferable target cancers are liver cancer, osteosarcoma, and the like.

The present invention is further illustrated in more detail by the Examples below, which is not intended to limit the scope of the present invention.

Examples

1. Producing the "Non"Conditionally Replicating Adenovirus Vector (Ad.Aurora-LacZ) which Expresses LacZ Gene as a Marker Under Control of the Aurora Kinase Promoter and "Conditionally Replicating" Adenovirus Vector (Aurora.CRA) Specific to Cancers Which the Virus Proliferation is Controlled Depending on the Aurora Kinase Promoter Activities The Ad.Aurora-LacZ was produced for an initial verification test to detect whether expression of the target gene is induced specific in cancer. Subsequently, later verification test was performed by using Aurora.CRA produced for a main object of the present invention that "the Aurora.CRA can be used a cancer treatment agent" by detecting "effects of proliferation of the virus and induction of cell death specifically in cancers as well as the cancer treatment effects" wherein "the viruses are specifically (superiority) enhanced to proliferate specifically in cancer cells expressing the Aurora kinase at higher level, thereby the virus proteins specifically replicated specifically in cancer cells cause cell death specifically to the cancer cells, and continuously the proliferated viruses infect to and cause cell death to other cancer cells specifically (superiority) to kill the cancer cells specifically." These two kinds of the adenovirus vectors having different objectives and structures were produced as follows.

1.1 Isolation of the Aurora Kinase Promoter

Human Aurora-A (L) promoter (SEQ ID NO: 1; 1840 bp; −1486 to +354) was obtained by digesting pGL3-1486 (provided by Dr. Ueda, Yokohama City University) at MluI/BsmI restriction site and blunted. Human Aurora-A (S) promoter (SEQ ID NO: 2; 478 bp; −124 to +354) was obtained by amplifying from pGL3-1486 using PCR with the primer (sense: 5'-TCAGTAGGGCCCCAGCT-GTGGGACTGCCACAGGTCTGGCTGG-3' (SEQ ID NO: 5); anti-sense: 5'-ATCTAGTCTAGACAGCT-GCTCTAGCTGTAATAAGTAACAAGC-3' (SEQ ID NO: 6), and cloned into an appropriate plasmid vector, then digested at ApaI/XbaI restriction site, and blunted. Human Aurora-B (L) promoter (SEQ ID NO: 3; 2140 bp; −1779 to +361) was obtained by digesting pGL3-1879 at XhoI/HindIII restriction site and blunted. Human Aurora-B (S) promoter (SEQ ID NO: 4; 546 bp; −185 to +361) was obtained by digesting pGL-187 (provided by Dr. Kimura, Gifu University) at XhoI/HindIII restriction site and blunted. Those four promoters were used to produce the Ad.Aurora-LacZ and Aurora.CRA described below.

1.2 Producing the "Non"Conditionally Replicating Adenovirus Vector Plasmid (pAd.Aurora-LacZ) which Expresses LacZ Gene as a Marker Under Control of the Aurora Kinase Promoter Plasmid pHMΔPr-LacZ was digested with ApaI restriction enzyme, blunted, and treated with CIP enzyme. The four Aurora kinase promoters digested and blunted as described above were ligated to this plasmid vector to produce four kinds of shuttle vector plasmids, pHM.Aurora-A (S), pHM.Aurora-A (L), pHM.Aurora-B (S), pHM.Aurora-B (L) that express LacZ genes as markers under control of Aurora kinase promoters; Aurora-A (S), Aurora-A (L), Aurora-B (S) and Aurora-B (L), respectively.

These shuttle vector plasmids were sub-cloned into plasmid pAd.HM4 containing the E1 region defective adenovirus genome at I-CeuI/PI-SceI restriction enzyme site to produce four kinds of adenovirus vector plasmids, pAd.Aurora-A (S), pAd.Aurora-A (L), pAd.Aurora-B (S) and pAd.Aurora-B (L). Finally, as described below, these adenovirus vector plasmids were transfected into 293 cells to produce four kinds of the "non"conditionally replicating adenovirus vectors which expresses LacZ gene as a marker under control of each of the Aurora kinase promoter.

1.3 Producing the "Conditionally Replicating" Adenovirus Vector Plasmid (pAurora.CRA) Specific to Cancers which the Virus Proliferation is Controlled Depending on the Aurora kinase promoter activities Conditionally replicating plasmid (P1 plasmid in FIG. 1), pΔPr-wtE1A-CMV-E1BΔ55KD (Japanese Patent 4478775; Nagano S et al., Gene Ther., 12: 1385-1393, 2005), was digested with restriction enzyme NotI, blunted using T4DNA polymerase, and treated with the CIP enzyme. With the shuttle vector plasmids, each of the DNA fragments of the four kinds, of promoter sequences obtained in above 1.1 (human Aurora-A (L), human Aurora-A (S), human Aurora-B (L), and human Aurora-B (S); SEQ ID NO: 1 to 4) were ligated so as to be inserted at the upstream of the E1A of the pΔPr-wtE1A-CMV-E1BΔ55KD. The pAurora-A (L)-wtE1A-CMV-E1BΔ55KD, pAurora-A (S)-wtE1A-CMV-E1BΔ55KD, pAurora-B (L)-wtE1A-CMV-E1BΔ55KD, and pAurora-B (S)-wtE1A-CMV-E1BΔ55KD were obtained.

The necessary DNA fragment of the E1 region was digested from the obtained four kinds of the "conditionally replicating plasmid" (P1 plasmid) at I-CeuI/PI-SceI restriction sites, ligated to the I-CeuI/PI-SceI restriction sites of the "adenovirus vector plasmid" (FIG. 1, P3 plasmid) pAd.HM4, to produce the plasmid of the conditionally replicating adenovirus vector (CRA) in which the Aurora kinase promoter was integrated to the upstream of the E1A gene. By fusing with A "treatment (marker) gene cloning plasmid" (FIG. 1, P2 plasmid) in which CMV promoter and EGFP gene were inserted (Kamizono J. et al., Cancer Res. 65: 5284-5291, 2005) using a Cre enzyme, transforming to Escherichia coli DH5α, and culturing in a medium containing an antibiotic tetracycline, an Aurora kinase promoter depending conditionally replicating adenovirus vector plasmid (pAurora.CRA) having a unit that expressed the marker gene EGFP was produced. These obtained four kinds of the conditionally replicating adenovirus vector plasmids (pAurora.CRAs), pAdAurora-A (L)-wtE1A-CMV-E1BΔ55KD/CMV-EGFP, pAdAurora-A(S)-wtE1A-CMV-E1BΔ551(D/CMV-EGFP, pAdAurora-B(L)-wtE1A-CMV-E1BΔ55KD/CMV-EGFP, and pAdAurora-B(S)-wtE1A-CMV-E1BΔ55KD/CMV-EGFP have the region of adenovirus genome except for E1 and E3 regions, E1A region operably linked to the Aurora kinase promoter, E1B region operably linked to the CMV promoter, and EGFP coding sequence operably linked to the CMV promoter. The pAurora.CRA plasmids were transfected into the 293 cells as described below to produce an Aurora kinase depending conditionally replicating adenovirus vector (Aurora.CRA).

1.4 Producing the Adenovirus Vectors in the 293 Cells

<Producing the Non-Conditionally Replicating Adenovirus Vector which Expresses the LacZ Gene as a Marker Under Control of the Aurora Kinase Promoter>

The plasmids (pAd.Aurora-LacZ) obtained in above 1.2 were transfected into the 293 cells originated from the human feral stem cells to produce the four kinds of the "non"conditionally replicating adenovirus vectors (Ad.Aurora-A (L)-LacZ, Ad.Aurora-A (S)-LacZ, Ad.Aurora-B (L)-LacZ, and Ad.Aurora-B (S)-LacZ) which expressed the LacZ gene as a marker under control of the Aurora kinase promoters. As positive controls, adenoviruses which expressed LacZ under control of a constitutive expression promoter, a Rous sarcoma virus LTR (RSV) and CMV promoter (Ad.RSV-LacZ and Ad.CMV-LacZ) were produced. As a negative control, the adenovirus that was defective in the E1 region (AdΔE1) was produced.

<Producing the Conditionally Replicating Adenovirus Vector (Aurora.CRA) Dependent on the Aurora Kinase Promoter which the Adenovirus Proliferation was Induced Depending on the Aurora Kinase Promoter Activities>

The conditionally replicating adenovirus vector plasmids obtained by above 1.3 were transfected into the 293 cells to produce the four kinds of the conditionally replicating adenovirus vectors dependent on the Aurora kinase promoters, AdAurora-A(L)-wtE1A-CMV-E1BΔ55KD/CMV-EGFP, AdAurora-A(S)-wtE1A-CMV-E1BΔ55KD/CMV-EGFP, AdAurora-B(L)-wtE1A-CMV-E1BΔ55KD/CMV-EGFP, and AdAurora-B(S)-wtE1A-CMV-E1BΔ55KD/CMV-EGFP.

<Producing the Adenovirus Vector>

As described above, the non-conditionally replicating adenovirus vector and conditionally replicating adenovirus vector are totally different in its purposes, structures, and method of producing the adenovirus vector plasmids. However, the experimental processes for producing viruses after production of the adenovirus vector plasmid are the same. Thus, the virus is produced by transfecting each adenovirus vector plasmid into the 293 cells as details described below.

The 293 cells were cultured in 10% FBS added DMEM. The transfection was carried out in accordance with the calcium phosphate method (*Current Protocols in Molecular Biology*, John Wiley and Sons, Inc., 9.1.4-9.1.9, 1999). Specifically, 40 μg of the DNA in total, 20 μg of liner DNA containing the adenovirus genome and 20 μg of salmon sperm DNA (SIGMA), were added into 1.5 ml HEPES buffered saline solution (pH 7.1), to which 75 μl of 2.5 M $CaCl_2$ was added with stirring, and incubated at a room temperature for 30 minutes, which were then dropped onto the 293 cells in stirring the cell culture. After incubating the cells in a $CO_2$ incubator for 4.5 hours, the 293 cells were continued to culture in solid medium prepared by pouring equal volume mixed solutions of 10% FBS added α-MEM and 1% of agarose gel into incubation dish. When the adenoviruses were produced, the 293 cells were degenerated and produced plaques.

The plaques were confirmed in a week after the transfection. The plaques were collected with the solid medium, suspended into the medium, and stored at −80° C. (a virus seed solution).

Then, the obtained virus seed solution was repeatedly frozen and fused for 3 times to release the viruses from the cells, which were used to infect 293 cells during the cultivation. Degenerated cells were collected with the medium and used for infection to other 293 cells. Gradually increased the scale, and finally 293 cells in 40 of 15 cm-dishes were infected and the degenerated cells were collected with the medium. After the cell degeneration, the cells were collected with the medium and centrifuged at 1,000 rpm, and the supernatant was removed. The pellets were suspended into 24 mL of phosphate-buffered saline (PBS), and stored at 80° C.

This cell suspension was repeatedly frozen and fused for 3 times and centrifuged at 1,000 rpm to collect supernatants, which were subjected to cesium chloride density-gradient centrifugation initially at 35,000 rpm for an hour at 10° C., then at 35,000 rpm for 18 hours at 10° C. to obtain the band containing the viruses. The obtained virus solution was purified using a desalting column. By using a series of these processes, both of non-conditionally replicating adenovirus and conditionally replicating adenovirus can be produced, replicated, concentrated, and purified.

FIG. 2 shows the structures of the produced non-conditionally replicating adenovirus vector and conditionally replicating adenovirus vector.

2. Quantitative RT-PCR (qPCR) Analysis

The quantitative RT-PCR was used to analyze the endogenous expression of mRNA of the Aurora kinase in various cell strains.

Total RNAs were collected from various cells using the Sepasol Kit (Nacalai), and processed with a DNaseI. One μg of the total RNAs were reverse-transcribed using the SuperScriptII reverse transcriptase (Invitrogen) and random primer (Invitrogen). 1/100 of the obtained cDNA were subjected to real-time PCR using the DyNAmo™HS SYBR (trademark) Green qPCR kit (FINZYMES). The reaction conditions of the PCR were as below: 94° C. for 10 seconds; 40 cycles of 58° C. for 30 seconds and 72° C. for 30 seconds. The Rotor-Gene3000 (Corbett) was used for the reaction. The primer sequences were as below:

```
Aurora-A (220 bp):
sense:
                                    (SEQ ID NO: 7)
5'-TCTTTTGGGTGTTATTCAGTGGC-3', antisense:
                                    (SEQ ID NO: 8)
5'-TTTTCTGTTTTGATGCCAGTTCC-3';

Aurora-B (167 bp):
sense:
                                    (SEQ ID NO: 9)
5'-AGAACTCCTACCCCTGGCCCTAC-3', antisense:
                                    (SEQ ID NO: 10)
5'-ATGCTCCACGCCCTCCTTCTCT-3'.
```

The results are shown in FIG. 3. The amount of mRNA in each cell was corrected to the amount of mRNA of a type II polymerase gene and was showed as the ratio as compared with that in HeLa cells which is to be 1. The endogenous expressions of the Aurora-A and Aurora-B were significantly higher in parts of cancer cell strains shown in the left of the graphs and low in normal cell strains shown in the right of the graphs. The Aurora kinase promoters of the present invention were specifically and endogenously activated in part of the cancer cells.

3. Promoter Activity Assay

The promoter activities of the isolated Aurora kinase promoter were compared between cancer cell strains (HepG2 cells and HOS-MNNG cells) and a normal cell strain (WI-38 cells).

The promoter activities were detected by measuring β-galactosidase activities using the β-Galactosidase Enzyme Assay System (Promega). HepG2 cells (human liver cancer origin), HOS-MNNG cells (human osteosarcoma origin), or WI-38 cells (human fetal lung fibroblasts origin: normal control) were infected by the Ad.Aurora-A (L)-LacZ, Ad.Aurora-A (S)-LacZ, Ad.Aurora-B (L)-LacZ, Ad.Aurora-B (S)-LacZ, Ad. RSV-LacZ, and Ad.CMV-LacZ at MOI (multiplicity of infection) 10 for an hour, at MOI 100 for an hour, or at MOI 30 for 24 hours. With these conditions, each type of cells showed the almost same gene transfer efficiency without showing any cytotoxicity. The cells were collected after 48 hours of the adenovirus infection, and the β-galactosidase activities were measured using the above assay system according to the instruction for use by the manufacture. The activities were calculated in accordance with the standard curve of the β-galactosidase prepared from a determined concentration.

The results are shown in FIG. 4. In the HepG2 cells (hepatoblastoma strain) and the HOS-MNNG cells (osteosarcoma origin cells high β-galactosidase activities due to expression of LacZ under control of the Aurora kinase promoters of the present invention (Aurora-A (L), Aurora-A (S), Aurora-B (L), and Aurora-B (S)) were confirmed. In the normal cells, WI-38 cells, β-galactosidase activity due to expression of LacZ under control of the Aurora kinase promoters of the present invention were not detected. On the contrary, when Ad.CMV-LacZ that expressed the LacZ under control of the CMV promoter was infected into the cells, β-galactosidase activities were detected in any cell strains.

From the above findings, the Aurora kinase promoter used in the present invention was shown to be specifically activated in the cancer cells to express the downstream gene. As shown in FIG. 3, the Aurora kinase is endogenously expressed a little in normal cells including the WI-38, and thus it was demonstrated that the Aurora kinase can show significantly higher level of specificity to cancers in using the extracted appropriate region as a promoter for expression of the exogenous gene, which is much superior to the specificity to cancers shown by expression patterns of the endogenous Aurora kinase gene. In other words, such significantly higher specific expression of the exogenous gene in cancer cells by using the Aurora kinase promoter could not be predicted simply from the endogenous expression patterns of Aurora kinase.

4. Cytotoxic Effect In Vivo

Cytotoxic effects by the virus vector of the present invention having the Aurora kinase promoter were assessed.

Cell viabilities were quantified as below. The cells in a 96-well plate were infected by the four kinds of the Aurora.CRAs or AdΔE1 at MOI 0.01 to 1. On the 2 to 6 days after the adenovirus infection, the Cell Count Reagent SF (Nacalai tesque) was used according to the instruction manual provided by the manufacturer, and the cell viabilities were quantified by WST-8 assay. Simply, the WST-8 assay was based on detecting mitochondrial activities as color reactions by using a compound that was converted by mitochondrial enzyme to show the color. The absorption of the samples at 450 nm and that of at 690 nm as a reference were measured using the Microplate Reader Model 550 (Bio-Rad).

Figure 5:
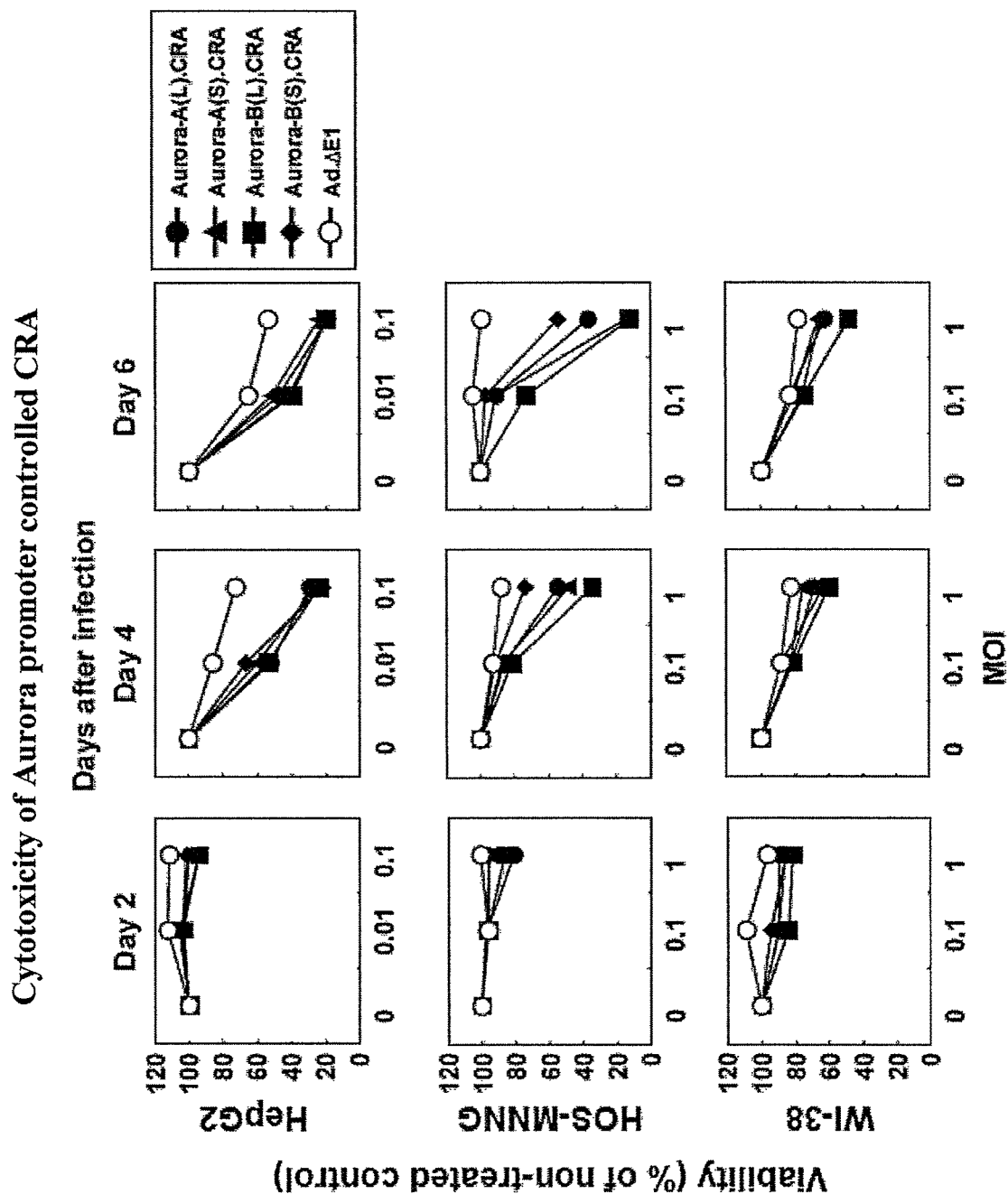
FIG. 5 is plots showing the cancer cells specific cytotoxic functions of the cancer specific conditionally replicating adenoviruses (CRAs) controlled by the Aurora promoters.

FIG. 5 shows the results of the cancer cell specific cytotoxicity. As markedly shown in results of 4-day of the HepG2 cells and 6-day of HOS-MNNG cells, these cancer cell strains infected with the conditionally replicating virus vector of the present invention showed a lower survival rate compared with the cells infected with the control AdΔE1 (replication defective adenovirus), which indicates cytopathic effects of the conditionally replicating virus vector of the present invention. On the contrary, the WI-38 cells hardly showed any differences between the control viruses and the viruses of the present invention.

Therefore, it has been clearly shown that the conditionally replicating virus vector of the present invention has the cytopathic effects specifically in cancer cells and is specifically capable of injuring cancers in vivo.

Figure 6:
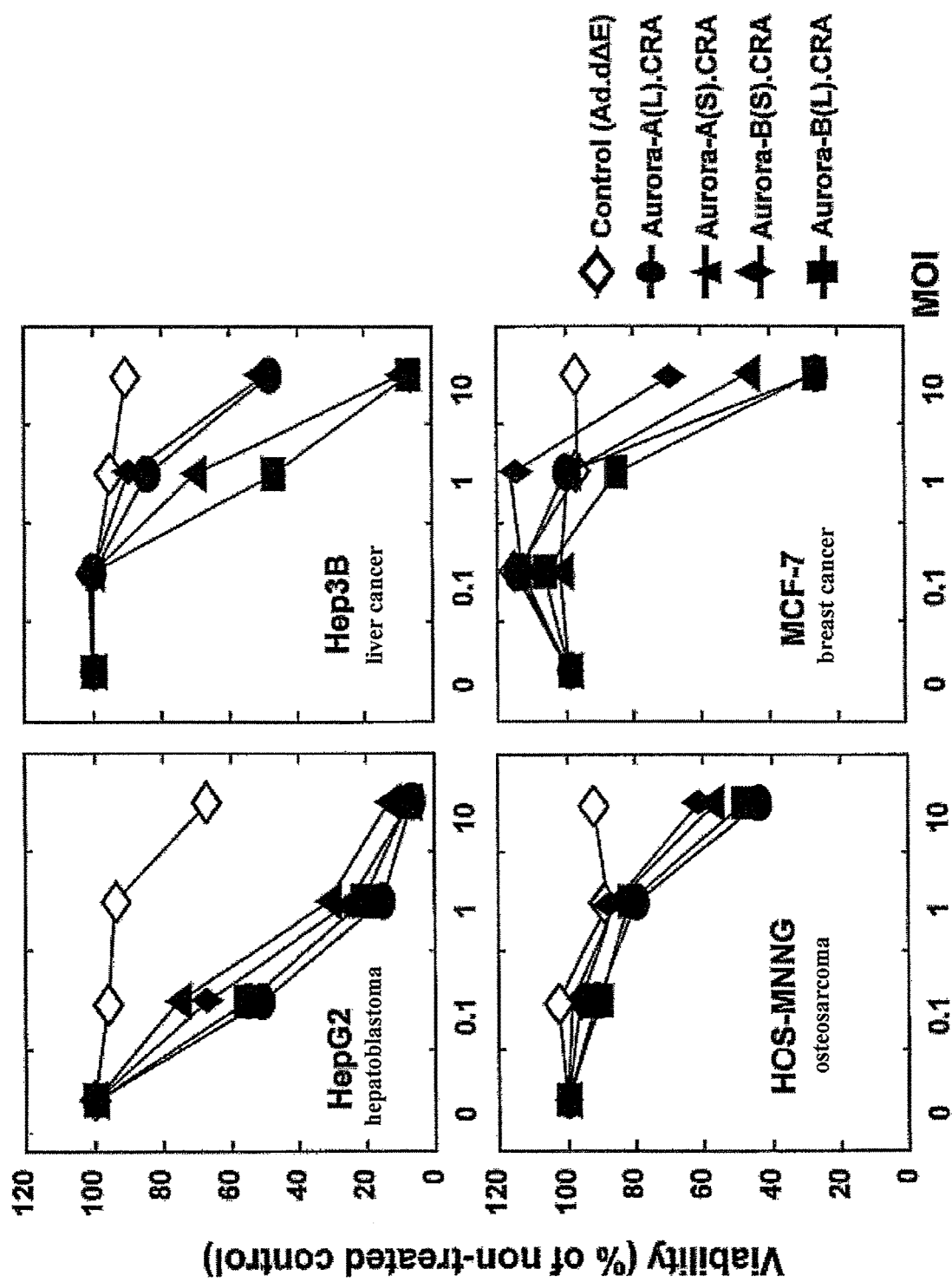
FIG. 6 is plots showing the cytotoxic functions of the cancer specific conditionally replicating adenoviruses (CRAs) controlled by the Aurora promoters to all types of cancer cells.

The same experiment was performed using a different liver cancer cell strain Hep3B cells, and a breast cancer cell strain MCF-7 cells, in order to confirm that this cytotoxic (cancer treatment) effect can be obtained in various cancers. The results are shown in FIG. 6. The cells were infected by each virus at MOI 0.01 to 10. On the 6-day, the cell viability was quantified using the WST-8 assay as well. Though the degree of the killing effect was different in each Aurora.CRA according to the types of cancer cells, all of the four kinds of Aurora.CRAs showed significant cytotoxic effects in cancer cells compared with the control (AdΔE1: replication defective adenovirus). This indicated that the conditionally replicating virus vectors of the present invention have the cytotoxic effects to overall cancers regardless of the types of cancer cells, and thus the virus vector can be used for a therapeutic agent for all types of cancers.

5. Treatment Effects in Cancer Model Animals

Figure 7:
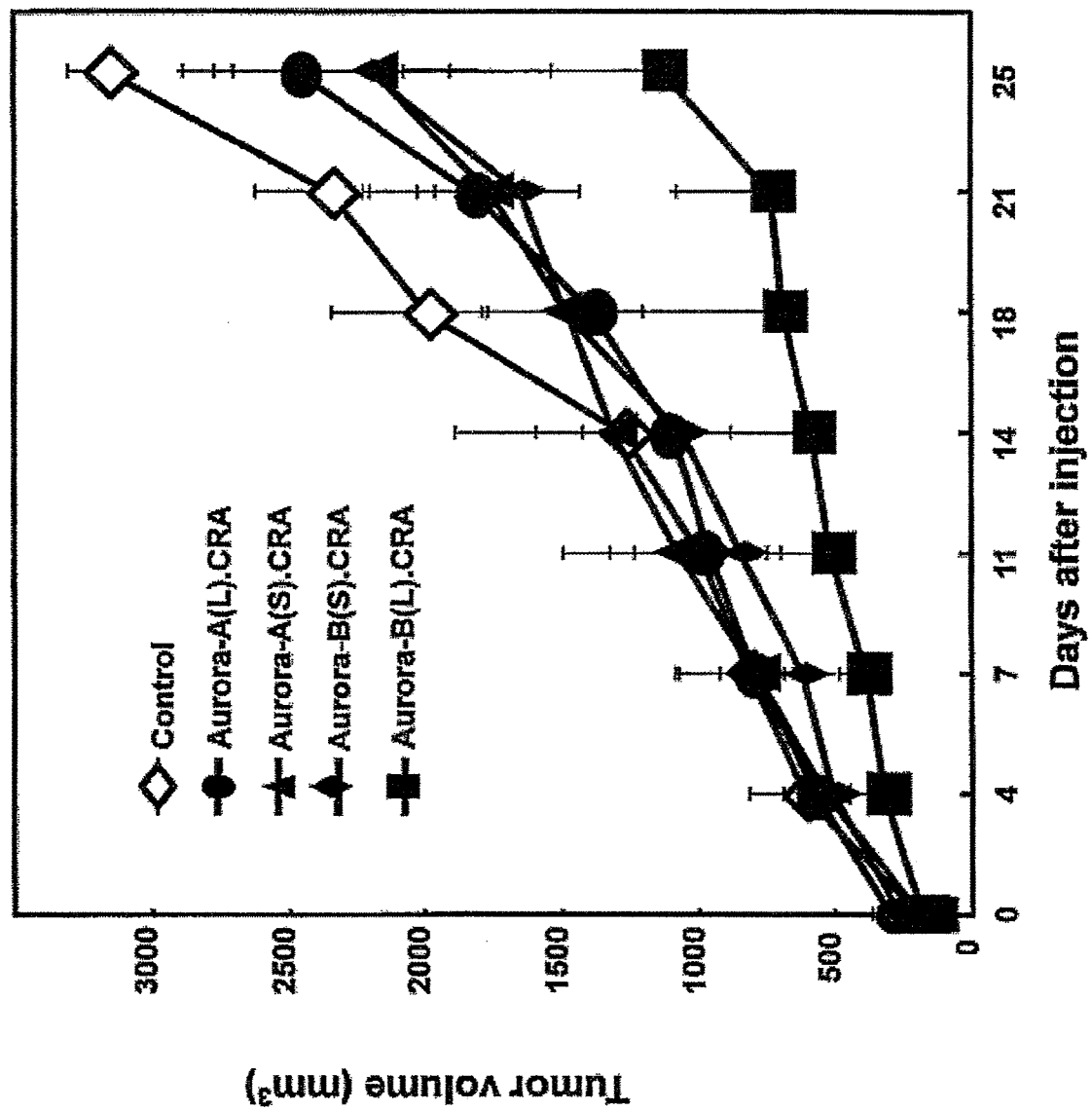
FIG. 7 is a graph showing the treatment effects of the cancer specific conditionally replicating adenoviruses (CRAs) controlled by the Aurora promoters in tumor animal models.

A pre-clinical cancer treatment effects were investigated using cancer model animals in order to confirm treatment effects for actual cancer diseases of all the four kinds of Aurora.CRAs. The liver cancer cells Hep3B ($10^7$ cells) (adjusted with PBS to the total amount of 200 µl) were subcutaneously injected into the left back of 8-week age female BALB/C nude mice. After the mass formation (7 to 12 mm), each virus was injected at $5.0 \times 10^8$ pfu/100 µl/tumor twice at interval of two days. After the second injection, the mass sizes were measured on the 4, 7, 11, 18, 21, and 25 days. On the 25 days, the mice were killed by euthanasia and the tumors (masses) were collected. FIG. 7 shows the course of the mass sizes. Any of the Aurora.CRAs showed significant suppression of the increases of the mass diameter (which means suppression effects for the tumor progression) compared with the control. The histopathological analysis was performed on the 25 days, and all of the Aurora.CRAs showed images of very significant cell death of the cancer cells whereas the control showed only partial death of the cancer cells. It is clear that all the Aurora.CRAs have tumor suppression effects compared with the control only from simple data of the mass diameter as shown in FIG. 6, but further data of histopathological images ensure the effects, which shows the masses of the mice treated with any of Aurora.CRA were mostly constituted of the dead cancer cells or bleeding associated with the cell death, whereas the masses of the control were mainly constituted of the survived cancer cells. The histopathological images show more significant cancer cell killing effects than that was shown in FIG. 6 as the masses sizes. This animal experiment clearly revealed that all the Aurora.CRAs have significant cancer treatment effects.

INDUSTRIAL APPLICABILITY

According to the present invention, a tool for high specific and effective cancer treatment is provided. Thus, the present invention has the industrial applicability in medical fields.

The aspects of preferred embodiments of the present invention were emphatically described. It will be clear to those skilled in the art that changes to the preferred embodiments may be made. The present invention intended that the present invention may be practiced other than as specifically described herein. The invention includes all the modifications included in the spirit and scope of the appended claims.

All references, containing publications, patent applications, and patents cited herein are hereby incorporated by reference to the same extent as if each reference were individually and specifically indicated to be incorporated by reference and were set forth in its entirety herein.

The present patent application is based on Japanese Patent Application No. 2010-223150 filed on Sep. 30, 2010. The disclosure of the Japanese Patent Application is incorporated herein by reference.

[Sequence Table Free Text]
SEQ ID NO: 1: human Aurora-A (L) promoter
SEQ ID NO: 2: human Aurora-A (S) promoter
SEQ ID NO: 3: human Aurora-B (L) promoter
SEQ ID NO: 4: human Aurora-B (S) promoter
SEQ ID NO: 5 to 10: primers

The invention claimed is:

1. A virus vector, wherein at least one promoter of a nucleic acid encoding a factor which is necessary for replication or assembly of a virus is substituted by an Aurora kinase promoter, wherein the virus vector is a cytolytic virus vector, and wherein the virus vector is specifically replicative in cancerous cells, but not in non-cancerous cells, wherein the Aurora kinase promoter comprises nucleotides 1363 to 1840 of the nucleotide sequence of SEQ ID NO: 1 or nucleotides 1595 to 2140 of the nucleotide sequence of SEQ ID NO: 3.

2. The virus vector according to claim 1, wherein the Aurora kinase promoter is a promoter of the human Aurora kinase A gene.

3. The virus vector according to claim 1, wherein the Aurora kinase promoter is a promoter of the human Aurora kinase B gene.

4. The virus vector according to claim 3, wherein the promoter of a human Aurora kinase B gene is a promoter consisting of the nucleotide sequence of SEQ ID NO:3.

5. The virus vector of claim 1, wherein at least one promoter of a nucleic acid encoding a factor which is necessary for a replication or assembly of virus is substituted with an exogenous promoter other than the Aurora kinase promoter.

6. The virus vector of claim 1, wherein at least one of the factors which is necessary for replication or assembly of virus is selected from the group consisting of: E1A, E1AΔ24, E1B, and E1BΔ55K.

7. The virus vector of claim 1, wherein the virus vector comprises an expression cassette including the Aurora kinase promoter or an exogenous promoter other than the Aurora kinase promoter which is operably linked to nucleic acids encoding cytotoxic or treatment factors.

8. The virus vector according to claim 5, wherein the exogenous promoter other than the Aurora kinase promoter is the promoter of a factor which expression is specifically enhanced in an organ, the promoter of a factor which expression is specifically enhanced in cancer cells, or the promoter which can be constitutively expressed in mammals.

9. The virus vector of claim 8, wherein the promoter of the factor which expression is specifically enhanced in the organs is a promoter of albumin, α-fetoprotein, prostate-specific antigen (PSA), mitochondrial form creatine kinase (MCK), myelin basic protein (MB), glial fibrillary acidic protein (GFAP), or neuron-specific enolase (NSE).

10. The virus vector of claim 8, wherein the promoter of the factor which expression is specifically enhanced in the cancer cells is a promoter of telomerase reverse transcriptase (TERT), carcinoembryonic antigen (CEA), hypoxia responsive element (HRE), Grp78, L-plastin, hexokinase II, or survivin.

11. The virus vector of claim 8, wherein a promoter which can be expressed in mammals is a cytomegalovirus early gene promoter (CMV).

12. The virus vector of claim 1, wherein the cytolytic virus vector is an adenovirus vector.

13. A therapeutic agent for treating cancer comprising the vector of claim 1.

14. A diagnostic agent comprising a vector of claim 1.

15. The diagnostic agent according to claim 14, which is for a diagnosis of cancer.

16. The virus vector of claim 6, wherein at least one of the factors which is necessary for replication or assembly of virus is selected from the group consisting of: E1A and E1AΔ24.

17. The virus vector of claim 2, wherein at least one promoter of a nucleic acid encoding a factor which is necessary for a replication or assembly of virus is substituted with an exogenous promoter other than the Aurora kinase promoter.

18. A virus vector, wherein at least one promoter for nucleic acids encoding a factor which is necessary for replication or assembly of virus is substituted by an Aurora kinase promoter, wherein the virus vector is a cytolytic virus vector, wherein the virus vector is specifically replicative in cancerous cells, but not non-cancerous cells, wherein the Aurora kinase promoter comprises bases of 1595 to 2140 of the nucleotide sequence of SEQ ID NO: 3, wherein at least one of the factors which is necessary for replication or assembly of virus is selected from the group consisting of: E1A, E1AΔ24, E1B, and E1BΔ55K.

19. A virus vector, wherein at least one promoter for nucleic acids encoding a factor which is necessary for replication or assembly of virus is substituted by an Aurora kinase promoter, wherein the virus vector is a cytolytic virus vector, wherein the virus vector is specifically replicative in cancerous cells, but not non-cancerous cells, wherein the Aurora kinase promoter comprises bases of 1363 to 1840 of the nucleotide sequence of SEQ ID NO: 1, wherein at least one of the factors which is necessary for replication or assembly of virus is selected from the group consisting of: E1A, E1AΔ24, E1B, and E1BΔ55K.

* * * * *

SEQUENCE LISTING

```
<160> NUMBER OF SEQ ID NOS: 10

<210> SEQ ID NO 1
<211> LENGTH: 1840
<212> TYPE: DNA
<213> ORGANISM: Homo sapiens
<220> FEATURE:
<223> OTHER INFORMATION: human Aurora-A(L) promoter

<400> SEQUENCE: 1
tcacatgaga gattagaggc tgacaccacc cagaagatca cctattctgt ctgcataaca      60
aacttgattc accatacatt tcctccgttc accgtcccat aacttgtgtt agagctgctt     120 cccgccccc  gcccccaatt ctctattcat tcctttcagt agctcaggat gccatgtagg     180
ctttaatcat ctgacttcaa cttttagtct cgtattttgt gggactcctg tacgtaatta     240
aatatcgttt ttctcccatg gacaatgttc agttacccga aaaaatggg  agattcttaa     300 ggtaccaata aagaatgaaa atcacaagtg ggtagtctgg caaagaaaag ttgatgagag     360
attctactgt taacgttggg ttaatatgac tcgaataatt tccgtatgct agctcaatgc     420
tttacatgca catcctgttt accctgcagt aatctgttaa ttcgtcttat gtgaatttaa     480
ctctttgtcc taataaggta cctggaagga tggagggaag ccattttttgg ttcccctaca    540 ccactgttct atccggtctc ttcacttctg ctgagcacat cccgggtgta catatacaca     600
cacacacaca catatatgtg tgtgtatata tatgtatatg tgtgtgtgtg tatatatata     660
tatatatatt ttaagtggcc caccctaac  ttctcaactc ccacagaacg ttcactcgcc     720
aggtaaacag aagcctaatt atccccaatt tgcaggtcag cacacgagga caagaacccg     780
atccaggacc ggatacatcg cagttggaaa ggctagaaca cagatgcccc ctcactatat     840
cgccgcgacc atctggatgc agaggcgaac taaggactgg gtgggaatgg aagcgaggcc     900
cttcgagaag aggaaggggt gcaggccagc cgggcaactt aggaaacaca aagtagaggc     960
gcatgccacc ttgctaactc tcgactcttc cagtctcgcc ccagtcgttt ctgtggtttt    1020
ctctaaatgc cccagccgac cgcaccagct actctccccg tgtcccagca ccagctggtc    1080
cggttctctt ggtatcccgc tctctcctgg aaaaatggag gcgcgaatcc tgcccaatct    1140
accgctccga gcgcacgttc actgcgcacg ctgaaagggc gccaagccga ccgctgcgct    1200
atcgatcggt cccactctct cttgcttttc tcgccatctt acttactggc acgttcaaag    1260
gttagttcac ctcctcggac tttatctcca atgcgtcaag cttgacgtca aggggctgtt    1320
gcttcaccga taaatggccg accgcggaga gcacctgggg gctgggactg ccacaggtct    1380
ggctggccgt tggctccacc acttccgggt tcttagggag caagtcgcct gcgcgcggtg    1440
```

-continued

| | |
|---|---|
| tgcgcccttaa aacgcgactc aaggcgtcgg gtttgttgtc aaccaatcac aaggcagcct | 1500 |
| cgctcgagcg caggccaatc ggctttctag ctagagggtt taactcctat ttaaaaagaa | 1560 |
| gaacctttga attctaacgg ctgagctcct ggaagacttg ggtccttggg tcgcaggtgg | 1620 |
| gagccgacgg gtgggtacac cgtgggggat atctcagtgg cggacgagga cggcggggac | 1680 |
| aaggggcggc tggtcggagt ggcggagcgt caagtccctg tcggttcctc cgtccctgag | 1740 |
| tgtccttggc gctgccttgt gcccgccag cgcctttgca tccgctcctg ggcaccgagg | 1800 |
| cgccctgtag gatactgctt gttacttatt acagctagag | 1840 |

<210> SEQ ID NO 2
<211> LENGTH: 478
<212> TYPE: DNA
<213> ORGANISM: Homo sapiens
<220> FEATURE:
<223> OTHER INFORMATION: human Aurora-A(S) promoter

<400> SEQUENCE: 2

| | |
|---|---|
| tgggactgcc acaggtctgg ctggccgttg gctccaccac ttccgggttc ttagggagca | 60 |
| agtcgcctgc gcgcggtgtg cgcccttaaa cgcgactcaa ggcgtcgggt ttgttgtcaa | 120 |
| ccaatcacaa ggcagcctcg ctcgagcgca ggccaatcgg cttttctagct agagggttta | 180 |
| actcctattt aaaaagaaga acctttgaat tctaacggct gagctcctgg aagacttggg | 240 |
| tccttgggtc gcaggtggga gccgacgggt gggtacaccg tggggatat ctcagtggcg | 300 |
| gacgaggacg gcggggacaa ggggcggctg gtcggagtgg cggagcgtca agtccctgtc | 360 |
| ggttcctccg tccctgagtg tccttggcgc tgccttgtgc ccgccagcg cctttgcatc | 420 |
| cgctcctggg caccgaggcg ccctgtagga tactgcttgt tacttattac agctagag | 478 |

<210> SEQ ID NO 3
<211> LENGTH: 2140
<212> TYPE: DNA
<213> ORGANISM: Homo sapiens
<220> FEATURE:
<223> OTHER INFORMATION: human Aurora-B(L) promoter

<400> SEQUENCE: 3

| | |
|---|---|
| agtagcacta gaagcagcaa tgagggctgc atgcttccct gctcacttcc agaaatctct | 60 |
| tcctccatac cttgccctat acatcttttc atctatatca tttgtaatac actttatgat | 120 |
| aaaccagtaa acgttaagtg tttccttgag ctgcccagca ttctgagcaa gaaactgatt | 180 |
| cccactagct ggcccactta aatcacaggc ttatgcctga tccaataacc ataatctgga | 240 |
| ataaaaggta ttgattagta taagttaatt ggggctcatt tctggacctg caatgaagtc | 300 |
| agtttccttc tcaaatcctc aaaactctaa gtgctttcag aagtgggaat aaagctgggc | 360 |
| gcagtggctc acgcctgtaa tccaagcact ttgggagacc aaggcgggcg gatcacctga | 420 |
| ggccagcctg agcaatgtga tgaaaccccg tctctactaa aaatacaaaa attagccggg | 480 |
| cgtggtcaca tgcacctata atcctaggta ctcgggaggc tgagacagga gaatcagttg | 540 |
| caccctggag gaggaggttg tggtgagctg agattgtgcc attgcactcc agcctgggca | 600 |
| acacagcgaa tcttcatctc aaaaaaaaaa aaaaagtga gatttaaata ggtcttcatc | 660 |
| aacctaggga tttggggttg tcagcaacag aaactactac agaaaccgac tgcatagact | 720 |
| ggagagacag gtggtcccct aaaggaaaaa tagagtgtta aagaaaggaa aagagtgct | 780 |
| ggacagtaca tacttaataa atatccactg gttatttcat agaaggccca aaaatgtatt | 840 |
| tatttaaccc agtaatgaaa tctgagggtt aggaagagca gaaaagaagg aagtgtggca | 900 |

```
ggaaggagga aaaatgaaag tgggcccaaa caacacggca gctaacagag atcttgcaac      960
gaaaggtcta ttggtggaaa aactcctccc aggaatgtca gaacttttaa gaacgacata     1020
gtaatgacac aagaataaac acacaggcaa atgagcaaac aacggaatac aaagtctaga     1080
aatagacaca agtaaatatg ctaacattat atatcaaggg cagcatttaa attctgttgg     1140
ggcagtttgt ttaacaaatg gtgttgacat aactggcgct ccatcgggca gagaagttag     1200
accccagctc atacatgcat aaggataaac tccagttaca ttaaagattt aatttttttt     1260
ataaaaagaa gaaggccggg cacggtggct cacgcctgta atcccagcat tttgggaagc     1320
cgaggcgggt ggatcacctg aggacaggag ttcgagacca gattggccaa cacagcgaaa     1380
acccgtctct aataaaaata caaaaattag ccaggcgtgg tggcgggcgc ttgtaatccc     1440
agctactcgg gtggctgagg cacgagaatc gcttgaaccc gggaggcaga ggttgcagca     1500
agcccagata gcaccattat actccagcct gagcgacaga gagagacctg tctcaaaaaa     1560
ggaaaaaaaa aaagaaaaga aaaagcaaga taattcactg ggggaatttg gggaaacttt     1620
cctaaactgg aagccaagcg tgagcccttc tcattccgcc tcttccattg ggttcccatg     1680
acttacgtca caggacatcg agccaatggg aactaggcat gggcgacgag cttgcccaat     1740
ggggccgggg cgggagattt gaaaagtcct tggccagggc gcggcgtggc agattcagtt     1800
gtttgcgggc ggccgggaga gtagcagtgc cttggacccc aggtgagctg gcctcctgtc     1860
gcaggccttg cgccgggagt gggcagatga tcaggtagat cagagggtcc gttgggctgg     1920
cctgcgcgca cgccgcaggg ctggaaggag gtagggacga tagcagggcg ggggcggtga     1980
gaccagcgcc cagattgggg ctagtgtgct gacctgctcc cttttaccag ctcgggctag     2040
cgcttccggc tcgatcggtc caaccccctcc ctctctctct cttttctct gcttctcacg     2100 gctgtttccc ttctccgccc agctctcctc cccctttctc                          2140

<210> SEQ ID NO 4
<211> LENGTH: 546
<212> TYPE: DNA
<213> ORGANISM: Homo sapiens
<220> FEATURE:
<223> OTHER INFORMATION: human Aurora-B(S) promoter

<400> SEQUENCE: 4
tcactggggg aatttgggga aactttccta aactggaagc caagcgtgag cccttctcat       60
tccgcctctt ccattgggtt cccatgactt acgtcacagg acatcgagcc aatgggaact      120
aggcatgggc gacgagcttg cccaatgggg cggggcggg agatttgaaa agtccttggc       180
cagggcgcgg cgtggcagat tcagttgttt gcgggcggcc gggagagtag cagtgccttg      240
gaccccaggt gagctggcct cctgtcgcag gccttgcgcc gggagtgggc agatgatcag      300
gtagatcaga gggtccgttg gctggcctg cgcgcacgcc gcagggctgg aaggaggtag       360
ggacgatagc agggcggggg cggtgagacc agcgcccaga ttggggctag tgtgctgacc      420
tgctcccttt taccagctcg ggctagcgct tccggctcga tcggtccaac ccctccctct      480
ctctctcttt ttctctgctt ctcacggctg tttcccttct ccgcccagct ctcctccccc      540
tttctc                                                                 546

<210> SEQ ID NO 5
<211> LENGTH: 42
<212> TYPE: DNA
<213> ORGANISM: Artificial Sequence
<220> FEATURE:
```

```
<223> OTHER INFORMATION: primer

<400> SEQUENCE: 5
tcagtagggc cccagctgtg ggactgccac aggtctggct gg                              42

<210> SEQ ID NO 6
<211> LENGTH: 42
<212> TYPE: DNA
<213> ORGANISM: Artificial Sequence
<220> FEATURE:
<223> OTHER INFORMATION: primer

<400> SEQUENCE: 6
atctagtcta gacagctgct ctagctgtaa taagtaacaa gc                              42

<210> SEQ ID NO 7
<211> LENGTH: 23
<212> TYPE: DNA
<213> ORGANISM: Artificial Sequence
<220> FEATURE:
<223> OTHER INFORMATION: primer

<400> SEQUENCE: 7
tcttttgggt gttattcagt ggc                                                   23

<210> SEQ ID NO 8
<211> LENGTH: 23
<212> TYPE: DNA
<213> ORGANISM: Artificial Sequence
<220> FEATURE:
<223> OTHER INFORMATION: primer

<400> SEQUENCE: 8
ttttctgttt tgatgccagt tcc                                                   23

<210> SEQ ID NO 9
<211> LENGTH: 23
<212> TYPE: DNA
<213> ORGANISM: Artificial Sequence
<220> FEATURE:
<223> OTHER INFORMATION: primer

<400> SEQUENCE: 9
agaactccta cccctggccc tac                                                   23

<210> SEQ ID NO 10
<211> LENGTH: 22
<212> TYPE: DNA
<213> ORGANISM: Artificial Sequence
<220> FEATURE:
<223> OTHER INFORMATION: primer

<400> SEQUENCE: 10
atgctccacg ccctccttct ct                                                    22
```